US012691258B2

(12) United States Patent (10) Patent No.: US 12,691,258 B2
Ishida (45) Date of Patent: Jul. 28, 2026

(54) CATHETER ASSEMBLY

(71) Applicant: TERUMO KABUSHIKI KAISHA, Tokyo (JP)

(72) Inventor: Masahiro Ishida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1020 days.

(21) Appl. No.: 17/743,800

(22) Filed: May 13, 2022

(65) Prior Publication Data

US 2022/0265971 A1 Aug. 25, 2022

Related U.S. Application Data

(63) Continuation of application No. PCT/JP2020/042276, filed on Nov. 12, 2020.

(30) Foreign Application Priority Data

Nov. 14, 2019 (JP) ................................. 2019-206195

(51) Int. Cl.
*A61M 25/06* (2006.01)
*A61M 25/00* (2006.01)

(52) U.S. Cl.
CPC .... *A61M 25/0625* (2013.01); *A61M 25/0009* (2013.01); *A61M 25/0097* (2013.01);
(Continued)

(58) Field of Classification Search
CPC .......... A61M 25/0606; A61M 25/0631; A61M 25/0097; A61M 25/0618; A61M 25/0693; A61M 25/0643; A61M 5/3273
See application file for complete search history.

(56) References Cited

U.S. PATENT DOCUMENTS 5,009,642 A * 4/1991 Sahi ................... A61M 25/0643
604/110
5,743,882 A * 4/1998 Luther .............. A61M 25/0643
604/164.05
(Continued)

FOREIGN PATENT DOCUMENTS

CN 104302343 A 1/2015
CN 109475723 A 3/2019
(Continued)

OTHER PUBLICATIONS

Chinese Office Action issued in connection with CN Appl. Ser. No. 202080076208.5 dated Mar. 3, 2023.
(Continued)

*Primary Examiner* — Bhisma Mehta
*Assistant Examiner* — Adam J. Cermak
(74) *Attorney, Agent, or Firm* — Foley & Lardner LLP

(57) ABSTRACT

A catheter assembly includes: an inner and outer needle assembly including: a catheter hub holding the catheter, an inner needle inserted through the catheter and configured to be punctured into a treatment target, an inner needle hub holding the inner needle, and a safety member that is movable together with the catheter hub and configured to advance beyond a needle tip of the inner needle; and a grip that accommodates the inner and outer needle assembly. The grip is configured to accommodate at least a part of the safety member before puncture of the inner needle and until the safety member advances beyond the needle tip, and includes a first member and a second member that are dividable in a direction orthogonal to a longitudinal direction of the grip.

12 Claims, 19 Drawing Sheets

(52) U.S. Cl.

CPC .... *A61M 25/0606* (2013.01); *A61M 25/0637* (2013.01); *A61M 25/065* (2013.01)

(56) References Cited

U.S. PATENT DOCUMENTS

| | | | | |
|---|---|---|---|---|
| 6,210,379 | B1* | 4/2001 | Solomon | A61B 5/150641 604/164.01 |
| 6,221,050 | B1* | 4/2001 | Ishida | A61M 25/0606 604/167.03 |
| 10,384,039 | B2* | 8/2019 | Ribelin | A61M 25/09041 |
| 11,040,176 | B2* | 6/2021 | Blanchard | A61M 25/0606 |
| 2001/0018572 | A1* | 8/2001 | Kinsey | A61M 25/0643 604/164.08 |
| 2001/0025158 | A1* | 9/2001 | Chang | A61M 25/0643 604/170.02 |
| 2004/0030291 | A1* | 2/2004 | Holdaway | A61M 25/0643 604/164.08 |
| 2004/0116864 | A1* | 6/2004 | Boudreaux | A61M 25/0643 604/164.12 |
| 2007/0276288 | A1* | 11/2007 | Khaw | A61M 25/09041 604/164.13 |
| 2011/0282285 | A1* | 11/2011 | Blanchard | A61M 25/0097 604/164.08 |
| 2012/0053523 | A1* | 3/2012 | Harding | A61M 25/0612 604/164.08 |
| 2013/0023826 | A1* | 1/2013 | Ishida | A61M 5/158 604/165.02 |
| 2015/0231364 | A1* | 8/2015 | Blanchard | A61M 25/09041 604/164.08 |
| 2016/0089513 | A1* | 3/2016 | Ishida | A61M 25/0631 604/164.08 |
| 2016/0256667 | A1* | 9/2016 | Ribelin | A61M 25/09041 |
| 2016/0331938 | A1* | 11/2016 | Blanchard | A61B 5/1422 |
| 2017/0028171 | A1* | 2/2017 | Ishida | A61M 25/0668 |
| 2017/0028172 | A1* | 2/2017 | Ishida | A61M 25/0612 |
| 2017/0043132 | A1* | 2/2017 | Ishida | A61M 25/0606 |
| 2018/0008803 | A1* | 1/2018 | Muramatsu | A61M 25/0631 |
| 2018/0207406 | A1* | 7/2018 | Ishida | A61M 25/0631 |
| 2019/0298973 | A1* | 10/2019 | Shaw | A61M 25/0618 |
| 2020/0023167 | A1* | 1/2020 | Ishida | A61M 25/0068 |

FOREIGN PATENT DOCUMENTS

| | | |
|---|---|---|
| JP | 2003-512903 A | 4/2003 |
| JP | 2013-529111 A | 7/2013 |
| JP | 2016-214390 A | 12/2016 |
| JP | 2018-520722 A | 8/2018 |
| WO | WO-2016/152415 A1 | 9/2016 |

OTHER PUBLICATIONS

International Searching Authority, "Written Opinion," issued in connection with International Patent Application No. PCT/JP2020/042276, dated Dec. 22, 2020.

International Searching Authority, "Written Opinion" issued in connection with PCT Application No. PCT/JP2020/042276, dated Dec. 22, 2020, with English translation (8 pages).

International Searching Authority, "International Search Report," issued in connection with International Patent Application No. PCT/JP2020/042276, dated Dec. 22, 2020.

* cited by examiner

CATHETER ASSEMBLY

CROSS-REFERENCE TO RELATED APPLICATIONS

This is a bypass continuation of PCT Application No. PCT/JP2020/042276, filed on Nov. 12, 2020, which claims priority to Japanese Patent Application No. 2019-206195, filed on Nov. 14, 2019. The contents of these applications are hereby incorporated by reference in their entireties.

BACKGROUND

The present disclosure relates to a catheter assembly having a safety member that inhibits erroneous puncture of an inner needle.

When an introduction unit for infusion, blood transfusion, or the like is formed in a treatment target (patient), a catheter assembly, such as that disclosed in JP 2013-529111 A, is used. The catheter assembly includes a multi-piece tube in which an inner needle is inserted into a catheter (outer needle). When the catheter assembly is used, a user punctures the multi-piece tube into a body of the patient, then causes the catheter to enter a blood vessel, and further removes the inner needle from the catheter to indwell the catheter.

In addition, the catheter assembly disclosed in JP 2013-529111 A includes a safety member that moves following advancement and retraction of the catheter and covers a needle tip of the inner needle to activate an erroneous puncture inhibition function of the inner needle.

SUMMARY

The catheter assembly disclosed in JP 2013-529111 A activates the erroneous puncture inhibition function at a position where the safety member comes out of a grip held by a user during the operation. In such a configuration, when an external force, such as contact of the user, is applied to the safety member, the engagement of the safety member is relatively easily released to expose the needle tip. In addition, a mechanism of the safety member itself is complicated. Further, there is a possibility of infection when a needle body to which blood has been attached is touched.

In such a catheter assembly, it is also conceivable that the catheter assembly is configured such that the safety member does not come out of the grip and continues the erroneous puncture inhibition function (is continuously locked with the advancement and retraction being restricted). However, when the safety member is configured to be movable and continuously accommodated in the grip, an engagement structure between the respective members of the catheter assembly becomes complicated. As a result, the work of assembling the catheter, a catheter hub, the inner needle, an inner needle hub, the safety member, and the grip becomes complicated, work efficiency decreases, and there is a possibility that the members are damaged by undergoing a process such as forcible engagement.

Embodiments of the present invention have been developed in view of the above circumstances, and an object thereof is to provide a catheter assembly capable of simplifying assembly of each member and greatly improving work efficiency even in a configuration in which a safety member is continuously accommodated in a grip.

According to one aspect of the present invention, a catheter assembly includes: an inner and outer needle assembly in which a catheter, a catheter hub holding the catheter, an inner needle inserted through the catheter, an inner needle hub holding the inner needle, a safety member that is movable together with the catheter hub and advances beyond a needle tip of the inner needle stuck into a treatment target to activate an erroneous puncture inhibition function of the inner needle are assembled; and a grip which accommodates the inner and outer needle assembly. The grip is configured to accommodate at least a part of the safety member from before puncture of the inner needle to activation of the erroneous puncture inhibition function, and includes a first member and a second member that are dividable in a direction orthogonal to a longitudinal direction of the grip. The second member is capable of fixing the inner needle hub from a separated state of the first member as the inner and outer needle assembly is arranged along an assembling direction of the first member, and makes the safety member undetachable as the first member is assembled after the arrangement of the inner and outer needle assembly.

Certain embodiments of the above-described catheter assembly can greatly improve work efficiency even in the configuration in which the safety member is continuously accommodated in the grip.

BRIEF DESCRIPTION OF DRAWINGS

FIG. 1 is a perspective view of a catheter assembly according to one embodiment of the present invention;

FIG. 9 is a perspective view of an upper grip as viewed from below;

FIG. 10 is a perspective view illustrating a lower grip;

FIG. 12 is a sectional view taken along line XII-XII of FIG. 5;

FIG. 16 is a first explanatory view illustrating the assembly procedure of the catheter assembly;

FIG. 18 is a third explanatory view illustrating the assembly procedure of the catheter assembly;

DETAILED DESCRIPTION

Hereinafter, embodiments of the present invention will be described in detail with reference to the accompanying drawings.

Figure 1:
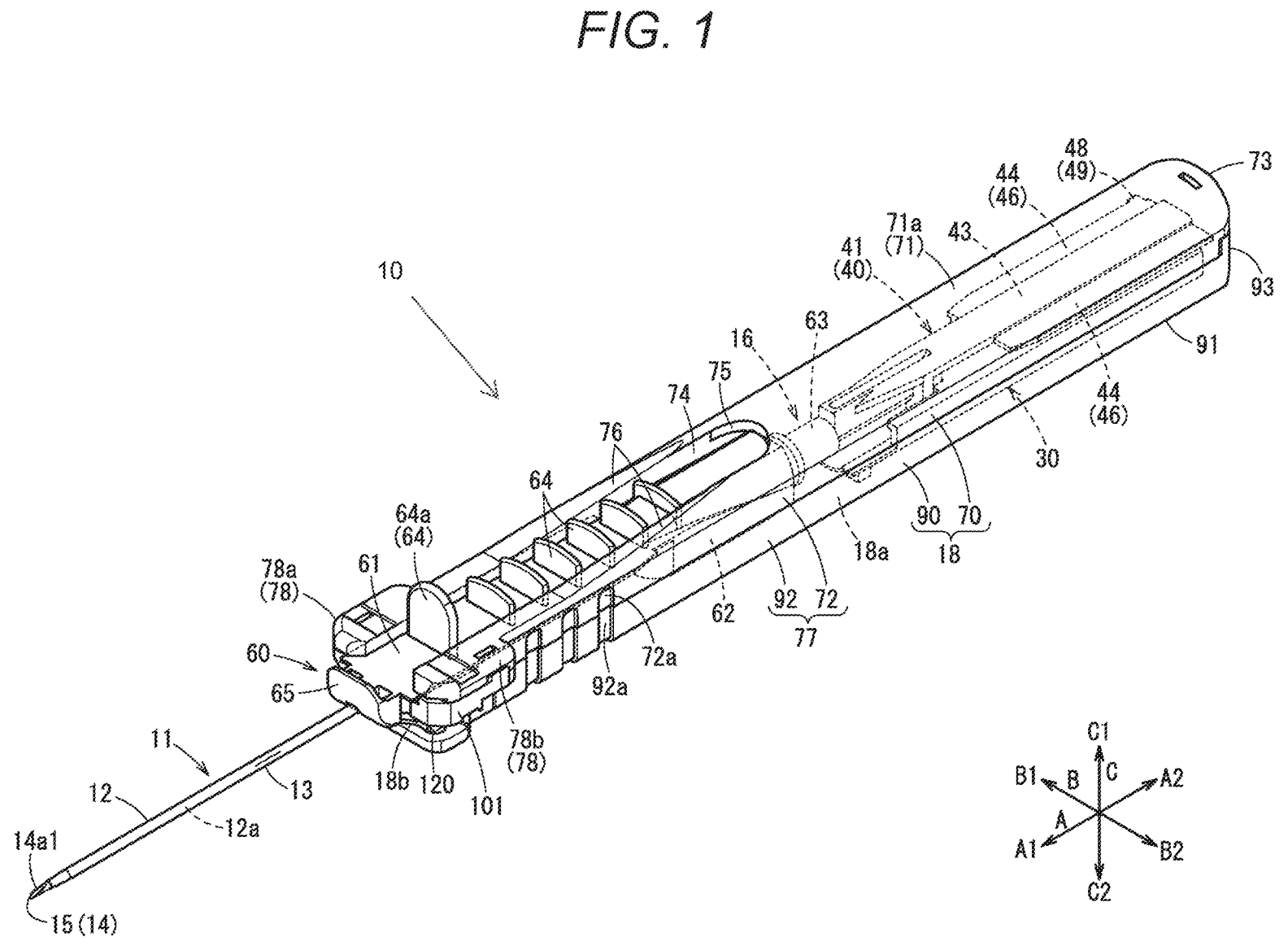

As illustrated in FIG. 1, a catheter assembly 10 according to an embodiment of the present invention is used at the time of performing infusion, blood transfusion, blood sampling, or the like on a treatment target (living body), and a catheter 12 is inserted into and indwelled inside the body of the treatment target to cause the inside and outside of the body to communicate. The catheter assembly 10 enables insertion of a catheter 12 having a longer length (for example, a central venous catheter, a PICC, a mid-line catheter, and the like) than a peripheral venous catheter. Incidentally, the catheter assembly 10 may also be configured to enable insertion of the peripheral venous catheter. In addition, the catheter assembly 10 is not limited to the venous catheter, and may be configured to enable insertion of an arterial catheter such as a peripheral arterial catheter.

Figure 2:
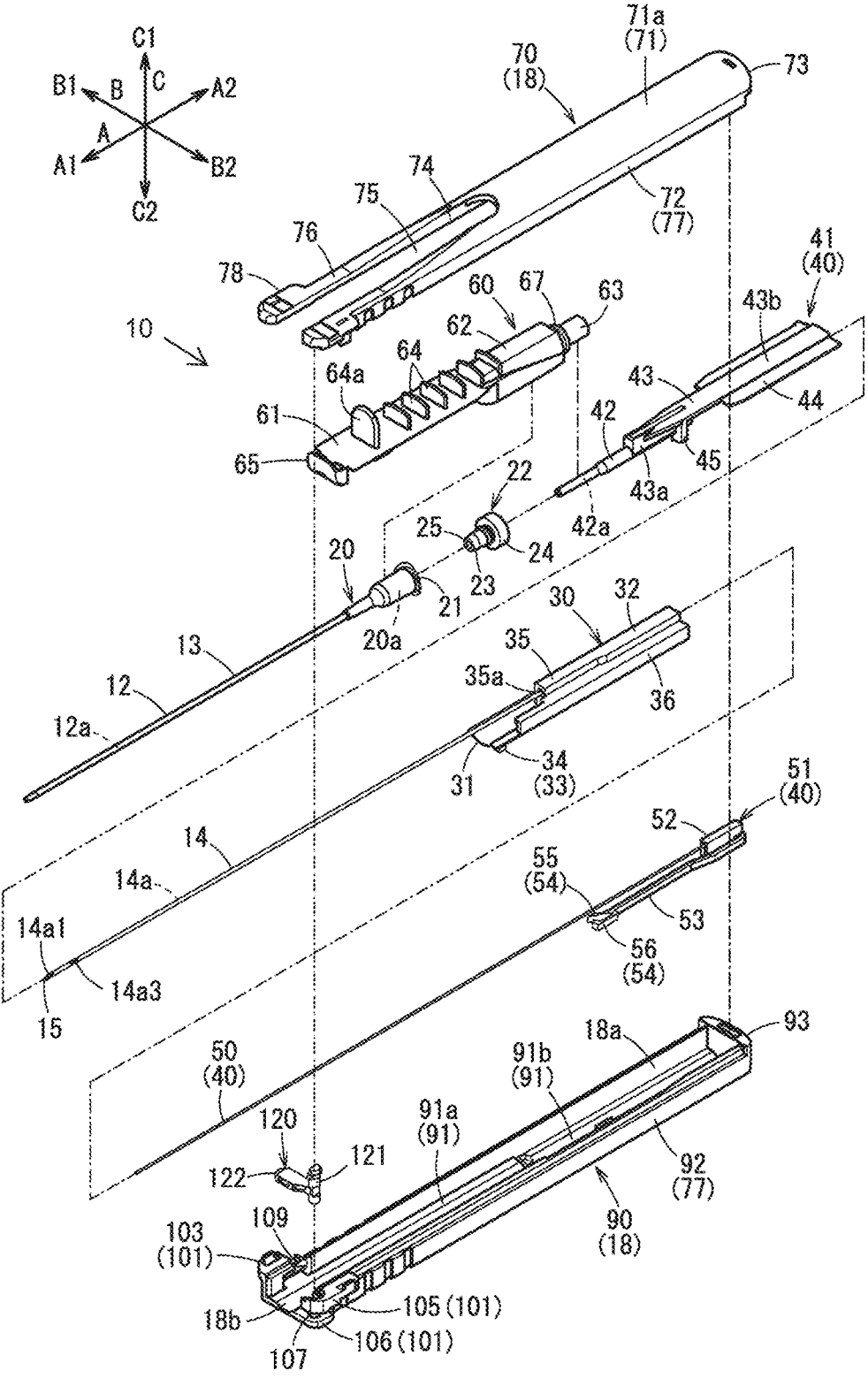
FIG. 2 is an exploded perspective view of the catheter assembly.

As illustrated in FIGS. 1 and 2, the catheter assembly 10 includes an inner and outer needle assembly 16 in which the catheter 12, an inner needle 14, a catheter hub 20, an inner needle hub 30, a safety member 40, and a catheter operation member 60 are assembled in a state before use (before puncture). Further, the catheter assembly 10 includes a grip 18 (housing) configured to accommodate the inner and outer needle assembly 16 and be gripped by a user.

In the inner and outer needle assembly 16 in the state before puncture, the inner needle 14 penetrates through the catheter 12 and the catheter hub 20 to form a multi-piece tube 11, and a needle tip 15 of the inner needle 14 protrudes from a distal end of the catheter 12. The safety member 40 through which the inner needle 14 is inserted is arranged closer to a proximal side than the catheter hub 20, and the inner needle hub 30 holding the inner needle 14 is arranged on the proximal side of the safety member 40. The catheter operation member 60 is arranged above the catheter 12, the catheter hub 20, and the safety member 40, and enables advancement and retraction of these members. A portion of the inner and outer needle assembly 16 located proximal of the multi-piece tube 11 is accommodated in the grip 18, and the inner needle hub 30 is fixed to the grip 18.

Figure 3A:
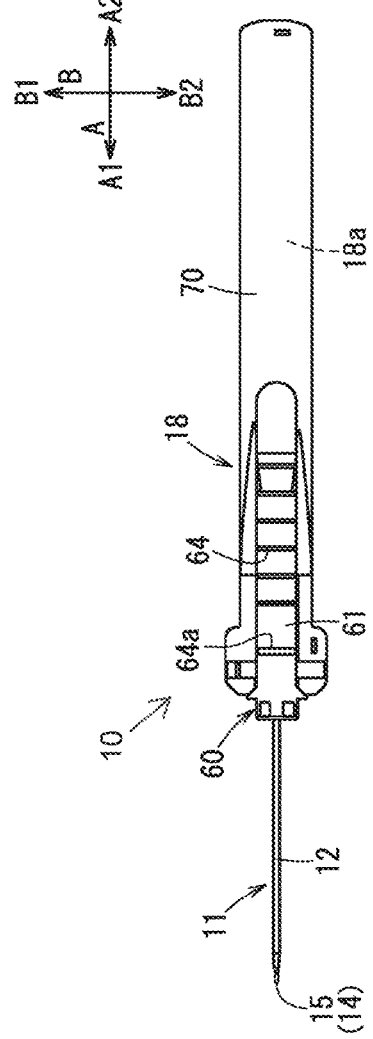
FIG. 3A is a first operation view illustrating a procedure at the time of using the catheter assembly.

First, operations at the time of using the catheter assembly 10 will be described in order to facilitate understanding of the catheter assembly 10 according to the present embodiment. At the time of use, the user, such as a doctor and a nurse, grips the grip 18 of the catheter assembly 10 in the state before puncture illustrated in FIG. 3A and punctures a blood vessel (vein or artery) of the patient (treatment target) with the catheter 12 and the inner needle 14. The user advances the catheter operation member 60 relative to the grip 18 (including the inner needle hub 30) to advance the catheter 12 and the catheter hub 20 while maintaining such a puncture state. As a result, the catheter 12 progresses to the depth of the blood vessel. At the initial stage of advancement of the catheter operation member 60, the safety member 40 also moves integrally with the movement of the catheter 12 and the catheter hub 20.

Figure 3B:
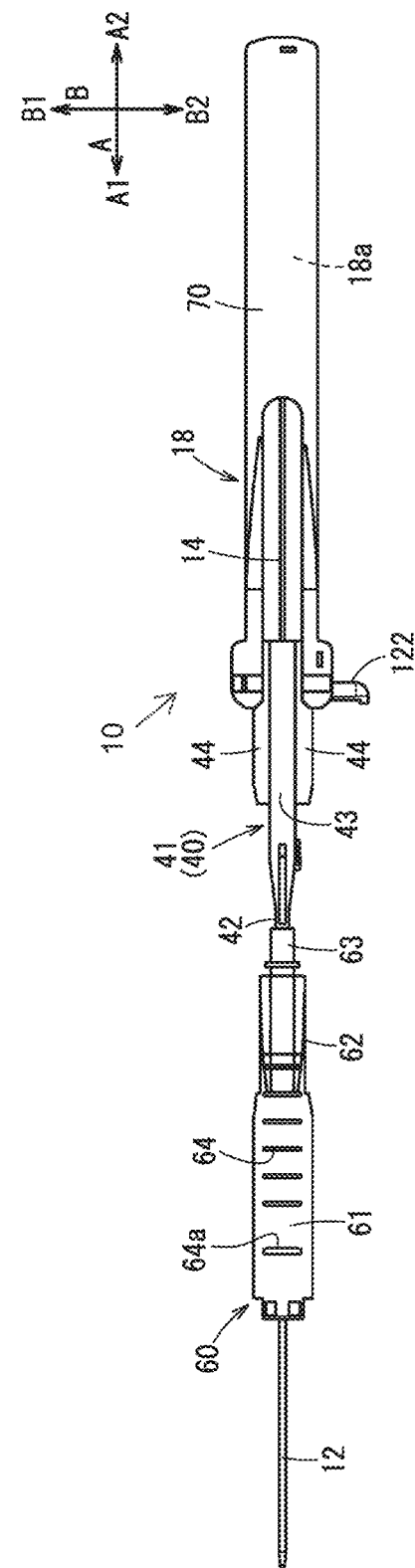
FIG. 3B is a second operation view illustrating a procedure at the time of using the catheter assembly.

As illustrated in FIG. 3B, the catheter 12 and the catheter hub 20 are removed from a distal end of the grip 18 by the above advancing operation, and the safety member 40 then protrudes from the distal end of the grip 18. Note that, the user may perform an operation of relatively retracting the grip 18 with respect to the catheter operation member 60 during the advancing operation of the catheter operation member 60 (the catheter 12 and the catheter hub 20). When the catheter operation member 60 is further advanced, a proximal end of the safety member 40 moves to a movement limit (advanced position) of the grip 18. At this time, a distal end of the safety member 40 is exposed from the grip 18 and advances beyond a distal end of the inner needle 14 to cover the inner needle 14, thereby activating an erroneous puncture inhibition function.

At the advanced position, the safety member 40 is in a locked state in which movement in both a distal direction and a proximal direction is stopped without coming out of the grip 18. As a result, when the catheter 12, the catheter hub 20, and the catheter operation member 60 are further advanced, the safety member 40 is separated from these members.

Figures 4A, 4B:
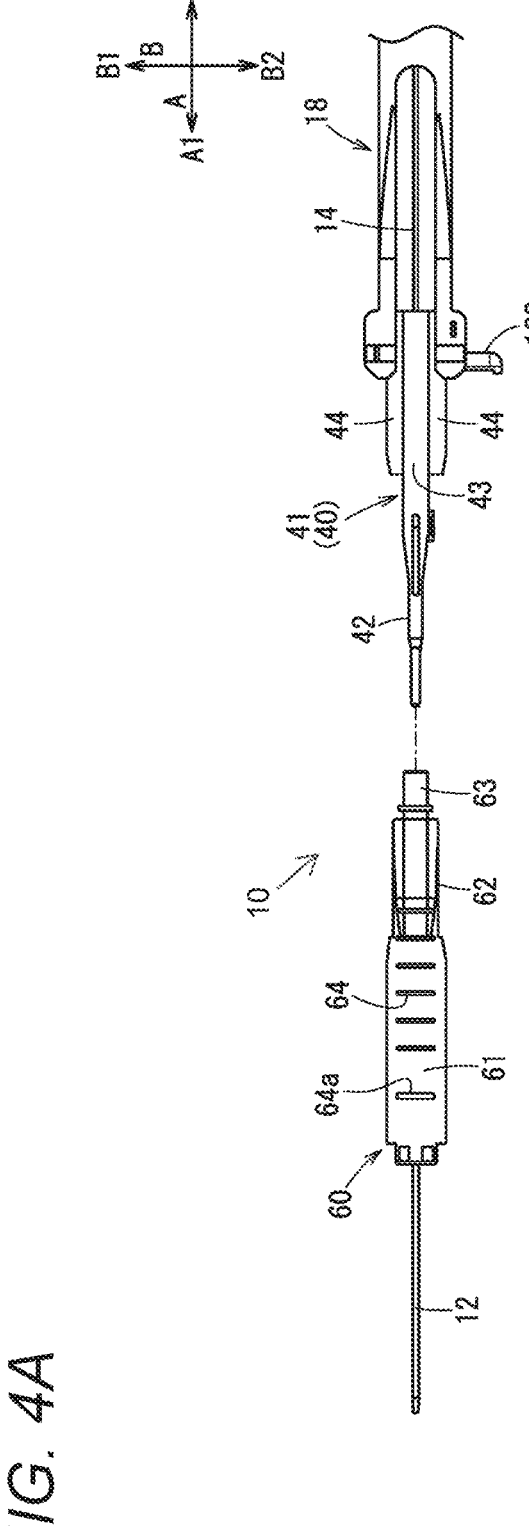
FIG. 4A is a third operation view illustrating a procedure at the time of using the catheter assembly.
FIG. 4B is a fourth operation view illustrating a procedure at the time of using the catheter assembly.

As illustrated in FIG. 4A, the engagement between the catheter operation member 60 and the catheter hub 20 can be released as the catheter operation member 60 and the safety member 40 are separated from each other in the catheter assembly 10. Therefore, the catheter 12 and the catheter hub 20 are separated from the lower side of the catheter operation member 60.

As illustrated in FIG. 4B, the catheter 12 and the catheter hub 20 are detached from the catheter operation member 60 and indwelled in the treatment target. Before the indwelling, a valve member 22 of the catheter hub 20 is removed, and a connector (not illustrated) of another medical device is connected. On the other hand, the inner needle 14, the inner needle hub 30, the safety member 40, and the grip 18 in the state of being integrated are appropriately discarded by the user. Hereinafter, the respective configurations of the catheter assembly 10 that implement the above operations will be specifically described.

Figure 5:
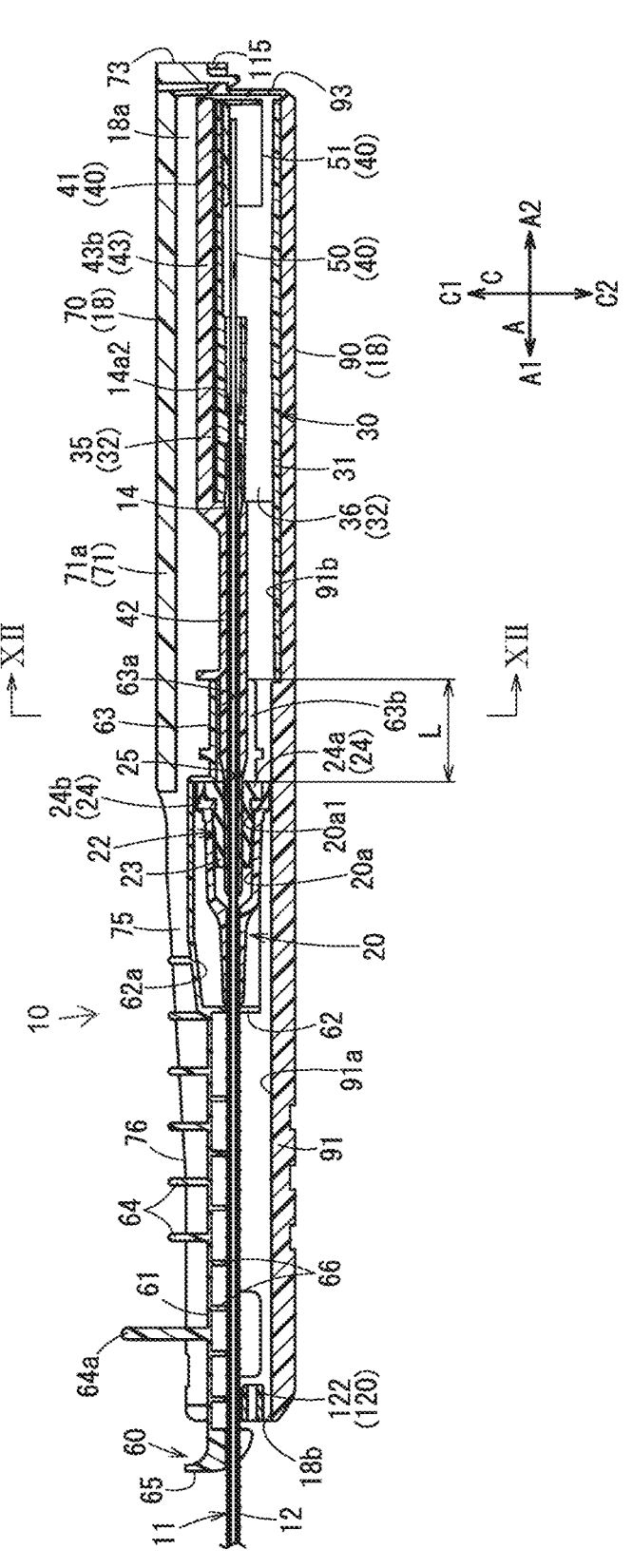
FIG. 5 is a side sectional view of the catheter assembly.
Figure 6A:
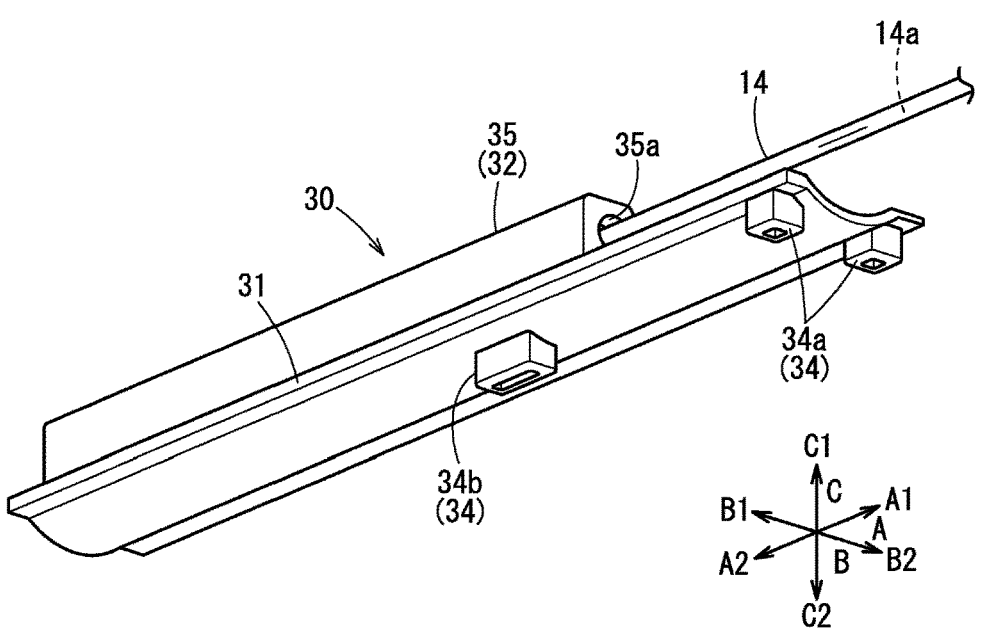
FIG. 6A is a perspective view of an inner needle hub that supports an inner needle as viewed from below.
Figure 6B:
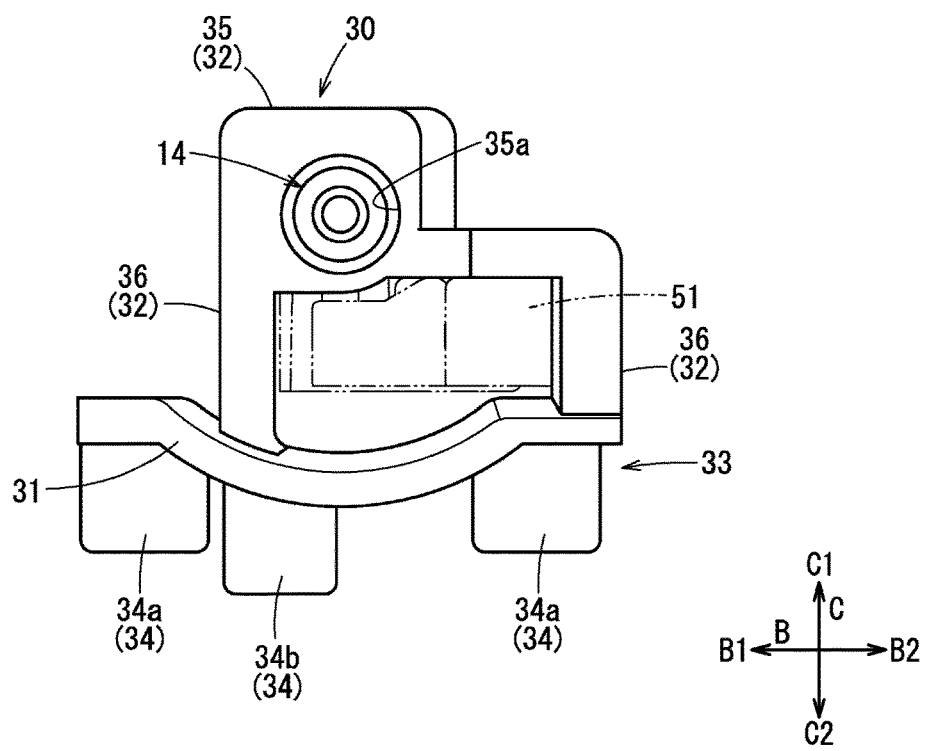
FIG. 6B is a front view of the inner needle hub that supports the inner needle.
Figure 7A:
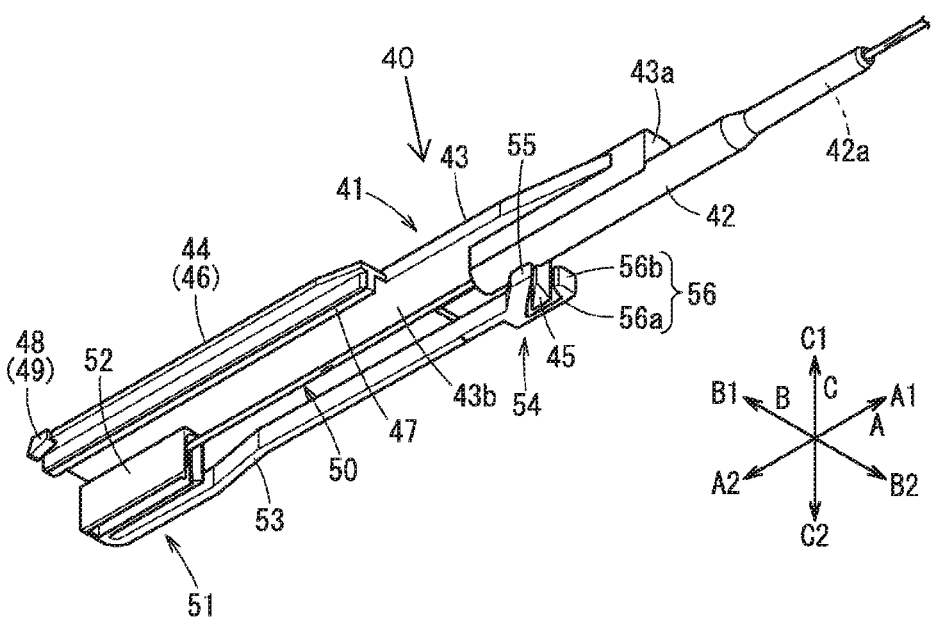
FIG. 7A is a perspective view of a safety member as viewed from below.
Figure 7B:
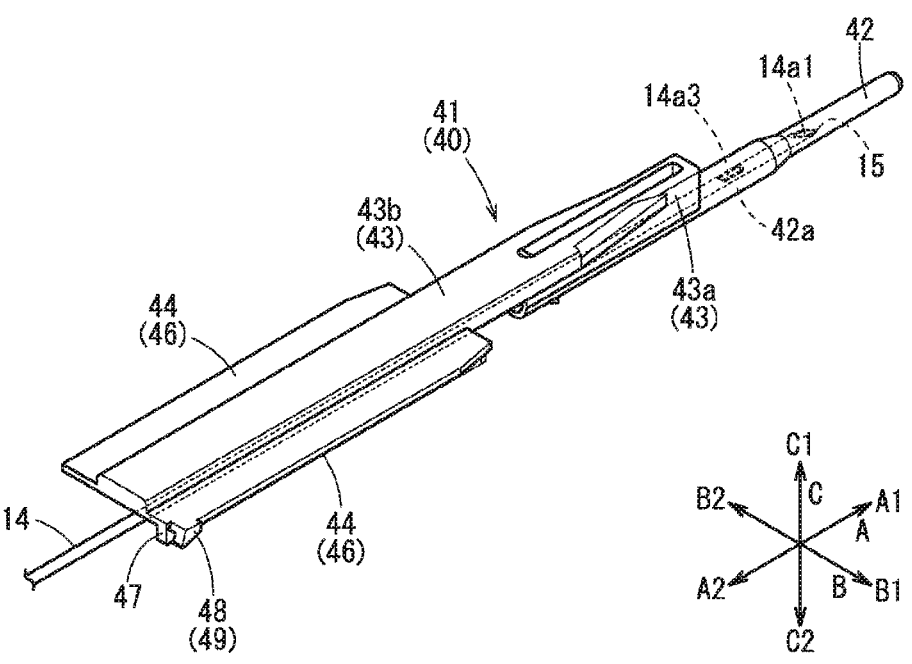
FIG. 7B is a perspective view illustrating a state in which a cover body covers the inner needle.

As illustrated in FIGS. 1, 2, and 5, the catheter 12 of the catheter assembly 10 is configured as a tubular body having appropriate flexibility. A lumen 12a penetrating in an arrow A direction (axial direction) is provided inside the catheter 12. The lumen 12a is set to have a diameter capable of accommodating the inner needle 14 and causing a medicinal liquid, blood, or the like to flow therethrough. A length of the catheter 12 can be appropriately designed according to use, various conditions, and the like, and is set to, for example, within a range of about 14 to 500 mm, is preferably set within a range of 30 to 400 mm, and is more preferably set within a range of 76 to 200 mm.

A suitable constituent material of the catheter 12 is a soft resin material, and examples thereof include a fluorine-based resin such as polytetrafluoroethylene (PTFE), ethylene-tetrafluoroethylene copolymer (ETFE) and perfluoro-alkoxy fluorine resin (PFA), an olefin-based resin such as polyethylene and polypropylene or a mixture thereof, polyurethane, polyester, polyamide, polyether nylon resin, a mixture of the olefin-based resin and ethylene-vinyl acetate copolymer, and the like.

The catheter 12 has an outer peripheral surface coated with a coating material 13 that reduces insertion resistance (puncture resistance) of the catheter 12 with respect to the treatment target. For example, the coating material 13 is preferably applied to the entire circumferential portion of the catheter 12 and to ⅔ or more of the entire length of the catheter 12 from the distal end to the proximal side (an arrow A2 side) of the catheter 12. In addition, the coating material 13 is also applied to the needle tip 15 of the inner needle 14 exposed from the distal end of the catheter 12. Note that the coating material 13 may also be applied to an inner peripheral surface forming the lumen 12a of the catheter 12, or may be applied to an outer peripheral surface of the inner needle 14.

A material constituting the coating material 13 is not particularly limited as long as the lubricity of the catheter 12 can be enhanced, and for example, a material capable of reducing frictional resistance, such as silicone, a maleic anhydride-based polymer, an acrylic acid-based polymer, and a sulfobetaine-based polymer, may be applied. In addition, a material that enhances hydrophilicity, water repellency, antibacterial property, or an antithrombotic property can also be applied as the coating material 13 in the catheter assembly 10.

A proximal end of the catheter 12 is fixed to a distal end in the catheter hub 20 by an appropriate fixing means such as caulking, fusion, and adhesion. The catheter hub 20 is exposed on a skin of a treatment target in a state in which the catheter 12 has been inserted into a blood vessel of the treatment target, and indwells together with the catheter 12 by being pasted with a tape or the like.

The catheter hub 20 is formed in a tubular shape tapered toward the arrow A1 side (distal direction). A flange 21 protruding radially outward is continuously provided on an outer peripheral surface on the proximal side of the catheter hub 20. The flange 21 has a spiral shape that enables screwing with another medical device. In addition, an internal space 20a that communicates with the lumen 12a of the catheter 12 and can cause the medicinal liquid or blood to flow is provided inside the catheter hub 20. A proximal end of the internal space 20a communicates with a proximal opening 20al of the catheter hub 20.

A constituent material of the catheter hub 20 is not particularly limited, but a thermoplastic resin such as polypropylene, polycarbonate, polyamide, polysulfone, polyarylate, and a methacrylate-butylene-styrene copolymer may be preferably applied, for example.

The valve member 22 is inserted into the catheter hub 20 from the proximal opening 20al to the back side (arrow A1 side) of the internal space 20a. The valve member 22 has an inserted portion 23 inserted into the catheter hub 20 and an exposed portion 24 exposed from the catheter hub 20. The inserted portion 23 is entirely made of an elastic material, and is formed in a tapered shape tapered toward the arrow A1 side. An outer peripheral surface of the inserted portion 23 can be brought into surface contact with an inner peripheral surface of the catheter hub 20.

The exposed portion 24 is continuous with a proximal end of the inserted portion 23 and is formed in a disk shape having an elastic portion 24a integrally molded with the inserted portion 23 and a hard portion 24b annularly covering the outer side of the elastic portion 24a. The radially outer side of the exposed portion 24 protrudes to the same extent as the flange 21 in a state in which the catheter hub 20 and the valve member 22 are assembled. A valve hole 25 that can be elastically opened and closed is provided at the axial center of the inserted portion 23 and the exposed portion 24. The distal ends of the inner needle 14 and the safety member 40 are inserted into the valve hole 25 in the state before puncture of the valve member 22, so that an inner surface of the valve hole 25 and an outer surface of the safety member 40 are in close contact with each other. As a result, the valve member 22 brings the catheter hub 20 and the safety member 40 into a fitted state, and inhibits leakage of blood at the time of puncture with the inner needle 14.

Meanwhile, the inner needle 14 of the catheter assembly 10 is configured as a hollow tubular body having rigidity so that the inner needle 14 is capable of puncturing a skin of a living body. The needle tip 15, which is sharp, is provided at the distal end of the inner needle 14. A hollow portion 14a is formed to penetrate the inside of the inner needle 14 along the arrow A direction, and the hollow portion 14a communicates with a distal opening 14a1 provided at the needle tip 15 and a proximal opening 14a2 provided at a proximal end of the inner needle 14. In addition, a lateral hole 14a3 that causes the outside of the inner needle 14 to communicate with the hollow portion 14a is provided at a position slightly away from the needle tip 15 to the arrow A2 side.

Examples of a constituent material of the inner needle 14 include a metal material such as stainless steel, aluminum or an aluminum alloy, and titanium or a titanium alloy, a hard resin, ceramics, and the like. The inner needle 14 is firmly fixed to the inner needle hub 30 by an appropriate fixing means such as fusion, adhesion, and insert molding.

As illustrated in FIGS. 2, 5, 6A, and 6B, the inner needle hub 30 includes a grip fixing portion 31 fixed to the grip 18, and a holding frame portion 32 protruding upward (toward the arrow C1 side) from the grip fixing portion 31 and directly holding the inner needle 14. The grip fixing portion 31 has a width to be inserted into an accommodation space 18a of the grip 18 and is formed to have an arc-shaped cross section in which the central portion in the width direction is recessed downward along a bottom wall 91 of the grip 18. A lower surface of the grip fixing portion 31 is provided with a plurality of (three in the present embodiment) fixing protrusions 34 that protrude slightly in the downward direction and constitute an attachment mechanism 33 with the grip 18.

The plurality of fixing protrusions 34 include a pair of distal fixing protrusions 34a located on the distal side of the grip fixing portion 31 in the arrow A direction and arranged side by side in the width direction, and an intermediate fixing protrusion 34b located in the middle of the grip fixing portion 31 in the arrow A direction. The pair of distal fixing protrusions 34a is formed in a substantially cubic block, and the intermediate fixing protrusion 34b is formed in a substantially rectangular block that is long in the arrow A direction.

In addition, the holding frame portion 32 has a tubular portion 35, which extends by a predetermined length in the arrow A direction and fixes the inner needle 14, on the distal side. The tubular portion 35 has a hole 35a for insertion of the inner needle 14 at the axial center. The holding frame portion 32 supports the tubular portion 35 through a plurality of frame plates 36 protruding from an upper surface of the grip fixing portion 31 and extending in the arrow A direction. The respective frame plates 36 cause the tubular portion 35 to float, thereby forming a space in which a blunt needle hub 51, which will be described later, can slide. The proximal side of the tubular portion 35 in the holding frame portion 32 constitutes a space that defines a slide range of the blunt needle hub 51.

As illustrated in FIGS. 2, 5, 7A, and 7B, the safety member 40 is configured to follow the catheter hub 20 in the movement process by being inserted and fitted into the catheter hub 20 (valve member 22). The safety member 40 includes a cover body 41 that covers the outer side of the inner needle 14 along with advancement, a blunt needle 50 protruding from the needle tip 15 of the inner needle 14 after puncture, and the blunt needle hub 51 holding the blunt needle 50.

The cover body 41 includes a distal cover portion 42 located on the arrow A1 side, a proximal extending portion 43 connected to an upper portion of the distal cover portion 42 and extending by a predetermined length toward the arrow A2 side, and a pair of protruding portions 44 protruding outward in the width direction from the proximal extending portion 43. In addition, an engagement projection 45 with which the blunt needle hub 51 is engaged is provided on the arrow A1 side of the proximal extending portion 43 (a connection point with the distal cover portion 42).

The distal cover portion 42 is formed in a cylindrical shape in which a protective space 42a capable of accommodating the inner needle 14 is formed to penetrate therethrough. The distal cover portion 42 is formed in a thin tubular shape on the distal side and in a thicker tubular shape on the proximal side. An outer peripheral surface on the distal side of the distal cover portion 42 is inserted into and brought into close contact with the valve member 22 in the state before puncture, thereby being frictionally fitted to the catheter hub 20 including the valve member 22. A proximal end of the distal cover portion 42 faces a distal end of the holding frame portion 32 of the inner needle hub 30 in the state before puncture. The cover body 41 is designed such that the needle tip 15 is located on the proximal side of the most distal end of the distal cover portion 42 at the advanced position at which the movement of the cover body 41 is restricted by the grip 18.

The proximal extending portion 43 includes a coupling portion 43a protruding upward at the connection point with the distal cover portion 42, and a plate portion 43b extending from the coupling portion 43a to the proximal side and formed to be slightly wider than the coupling portion 43a. The coupling portion 43a hangs the distal cover portion 42 to define its height (in an arrow C direction) position. The plate portion 43b has a thickness that makes the safety member 40 rigid so as not to be deformed in the vertical direction or the width direction. The plate portion 43b extends to a proximal end in the grip 18 along an upper portion of the inner needle hub 30 (holding frame portion 32) in the state before puncture.

The pair of protruding portions 44 is formed in a plate shape thinner than the proximal extending portion 43, and extends between an intermediate portion of the proximal extending portion 43 in the arrow A direction and the proximal end. Each of the protruding portions 44 protrudes outward in the width direction (arrow B direction) from the inner needle hub 30 (grip fixing portion 31) and extends to a position near a side wall 77 of the grip 18 (see also FIG. 12). The respective protruding portions 44 constitute a guide mechanism 46 which guides the safety member 40 in the arrow A direction in cooperation with the grip 18 when the safety member 40 moves.

In addition, one protruding portion 44 (on an arrow B1 side) of the pair of protruding portions 44 is provided with a guided projection 47 that protrudes toward an arrow C2 side and extends along the arrow A direction. The guided projection 47 constitutes a part of the guide mechanism 46, and is arranged on the inner side of a lower side wall 92 on the arrow B1 side of the grip 18 (a lower grip 90) to prevent displacement of the safety member 40 in the width direction.

Further, the protruding portion 44 on the arrow B1 side has a locked protrusion 48 on the arrow B1 side (the outer side in the width direction) of the guided projection 47 and on the arrow A2 side of the protruding portion 44. The locked protrusion 48 is locked to a locking portion 109 of the grip 18 at the advanced position at which the safety member 40 has advanced, thereby constituting one of safety movement restricting mechanisms 49 that restrict the advancement and retraction of the cover body 41. The locked protrusion 48 will be described in detail later.

The blunt needle 50 of the safety member 40 is a rod member (round rod) configured to inhibit the inner needle 14 from being stuck into the catheter 12 or the living body, and is movably accommodated in the hollow portion 14a of the inner needle 14. A distal end of the blunt needle 50 is formed in a shape blunter than the needle tip 15 of the inner needle 14 (for example, to have a polished flat surface), and is arranged at a position near a proximal end of the lateral hole 14a3 in the hollow portion 14a of the inner needle 14 in the state before puncture.

That is, the blunt needle 50 constitutes the multi-piece tube 11 together with the catheter 12 and the inner needle 14 in the state before puncture. Then, the distal end of the blunt needle 50 is exposed from the needle tip 15 as the safety member 40 advances. A thickness of the blunt needle 50 preferably has a diameter slightly smaller than a diameter of the hollow portion 14a of the inner needle 14, and for example, preferably has an outer diameter set in a range of about 0.19 mm to 1.19 mm. A material constituting the blunt needle 50 is not particularly limited as long as sufficient hardness can be obtained, and examples thereof include stainless steel, a superelastic alloy such as a Ni—Ti-based alloy, a shape-memory alloy, a cobalt-based alloy, noble metal such as gold and platinum, a metal material such as a tungsten-based alloy, or a resin material having a predetermined hardness or more.

In addition, the blunt needle hub 51 is configured to be relatively movable with respect to the inner needle 14, the inner needle hub 30, and the grip 18 by fixing and holding the blunt needle 50 and engaging with the cover body 41. The blunt needle 50 advances and retracts following advancement and retraction of the blunt needle hub 51. The blunt needle hub 51 includes a blunt needle holding portion 52 that holds the blunt needle 50 and an arm portion 53 extending in the distal direction from a proximal end of the blunt needle holding portion 52.

The blunt needle holding portion 52 is formed in a block shape having a predetermined height in the vertical direction, and has an upper portion that fixes the proximal side of the blunt needle 50. The blunt needle holding portion 52 is arranged in a space on the proximal side of the tubular portion 35 of the holding frame portion 32 in the state before puncture. Therefore, when the blunt needle hub 51 advances with respect to the inner needle hub 30 and a distal end surface of the blunt needle holding portion 52 comes into contact with the proximal end surface of the tubular portion 35, the subsequent advancement of the blunt needle hub 51 is prevented.

The arm portion 53 extends by a predetermined length from the blunt needle holding portion 52 to the arrow A1 side, and the entire extending portion is configured to be elastically deformable in the width direction. An engagement portion 54 that engages with the engagement projection 45 of the cover body 41 in the state before puncture is provided at a distal end of the arm portion 53. The engagement portion 54 includes an inclined portion 55 located at a distal end, and a hook portion 56 that protrudes slightly from the inclined portion 55 to the arrow A1 side and sandwiches the engagement projection 45 with the inclined portion 55.

The inclined portion 55 protrudes toward the arrow A1 side and the arrow B1 side (inward in the width direction). The engagement projection 45 of the cover body 41 is formed in a triangular shape along the inclination of the inclined portion 55 in a plan sectional view, and is guided by the inclination of the inclined portion 55. The hook portion 56 includes a plate piece 56a that protrudes from a connection point with the inclined portion 55 to the arrow A1 side, and a protrusion 56b that protrudes slightly from a distal end of the plate piece 56a to the arrow B1 side and encloses (catches) the engagement projection 45 with the inclined portion 55. When the cover body 41 advances at a stage in which the movement of the blunt needle hub 51 is restricted (stage in which the blunt needle holding portion 52 abuts on the tubular portion 35), the plate piece 56a of the hook portion 56 is elastically deformed outward in the width direction to release the catch between the protrusion 56b and the engagement projection 45.

Note that the safety member 40 is not limited to the above configuration as long as erroneous puncture of the needle tip 15 of the inner needle 14 can be inhibited. For example, the safety member 40 may include only the cover body 41 without including the blunt needle 50 and the blunt needle hub 51.

Figure 8:
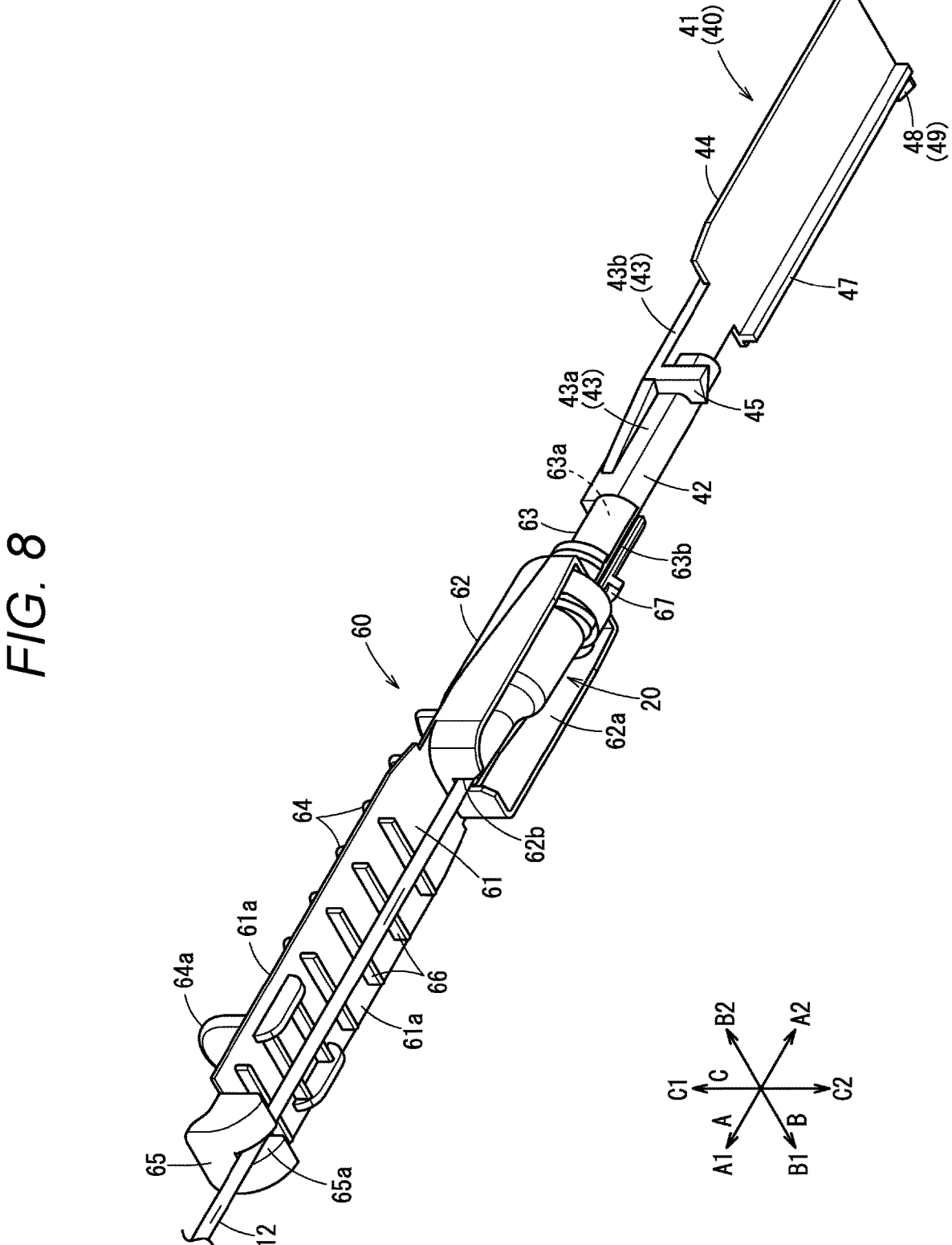
FIG. 8 is a perspective view of a state in which a catheter operation member is assembled to the catheter hub and the cover body as viewed from below.

As illustrated in FIGS. 2, 5, and 8, the catheter operation member 60 is a member that advances and retracts the catheter 12, the catheter hub 20, and the safety member 40 based on the user's operation. The catheter operation member 60 includes an operation plate portion 61 extending in the longitudinal direction (arrow A direction) of the grip 18, a hub accommodation portion 62 connected to a proximal end of the operation plate portion 61 and accommodating the catheter hub 20, and an operation member tubular portion 63 which is connected to a proximal end of the hub accommodation portion 62 and accommodates the safety member 40.

The operation plate portion 61 is a site in contact with a user's finger to perform an advancing/retracting operation. A plurality of tabs 64 are provided on an upper surface of the operation plate portion 61. A tab 64a at the most distal end among the plurality of tabs 64 protrudes more than the other tabs 64 to make the catheter operation member 60 to be easily pushed out by the user's finger. In addition, the operation plate portion 61 is formed to be thin and has flexibility so that the operation plate portion 61 is capable of being curved in a direction away from the multi-piece tube 11. A pair of side edges 61a of the operation plate portion 61 is arranged on a pair of rail walls 96 and 98, which will be described later, of the grip 18 in the state before puncture. A material from which the operation plate portion 61 (catheter operation member 60) is formed is not particularly limited, but, for example, the materials exemplified for the catheter hub 20 can be appropriately selected.

The operation plate portion 61 has a recessed block 65 extending toward the arrow A1 side and warped toward the arrow C1 side, at a distal end. A groove 65a in which the catheter 12 is arranged in a puncture state is provided in a lower surface of the recessed block 65 at the center in the width direction. A width of the groove 65a is formed to be slightly wider than an outer diameter of the catheter 12. A plurality of ribs 66 that can come into contact with the catheter 12 are provided on a lower surface of the operation plate portion 61.

Meanwhile, the hub accommodation portion 62 of the catheter operation member 60 has an accommodation chamber 62a for accommodating the catheter hub 20 including the valve member 22 on the inner side, and is formed in a box shape with the lower side of the accommodation chamber 62a opened. The hub accommodation portion 62 is formed to be narrower than the side wall 77 of the grip 18, and its movement is guided by the side wall 77 during the movement of the catheter operation member 60. The hub accommodation portion 62 has a gap 62b, which is narrower than the diameter of the catheter hub 20 and allows extension of only the catheter 12 (multi-piece tube 11), on a distal end surface.

The operation member tubular portion 63 is formed in a cylindrical shape that protrudes by a predetermined length from a proximal end surface of the hub accommodation portion 62 to the proximal direction. An insertion space 63a communicating with the accommodation chamber 62a of the hub accommodation portion 62 is provided inside the operation member tubular portion 63. The insertion space 63a is formed to penetrate through the inside the operation member tubular portion 63 in the axial direction, and the distal cover portion 42 of the safety member 40 (cover body 41) is inserted therethrough. In addition, the operation member tubular portion 63 includes an arcuate rib 67, which is formed to protrude in the circumferential direction and reinforces the operation member tubular portion 63, on an outer peripheral surface.

An inner diameter of the insertion space 63a is set to be slightly larger than an outer diameter D of the safety member 40 (the distal cover portion 42 of the cover body 41) and smaller than outer diameters of the catheter hub 20 and the valve member 22. Therefore, the operation member tubular portion 63 is configured to have a margin space 63a1 (see FIG. 12) with respect to the outer diameter D of the inserted distal cover portion 42. As a result, the safety member 40 is axially rotatable with respect to the catheter operation member 60.

The operation member tubular portion 63 has a slit 63b formed over the entire axial length of the operation member tubular portion 63. That is, the slit 63b communicates with the accommodation chamber 62a on the distal side, and linearly extends to the most proximal end of the operation member tubular portion 63. The slit 63b enables passage of the inner needle 14 from the side of the operation member tubular portion 63 to the insertion space 63a, and inhibits passage of the distal cover portion 42 from the insertion space 63a to the side of the operation member tubular portion 63.

Figure 12:
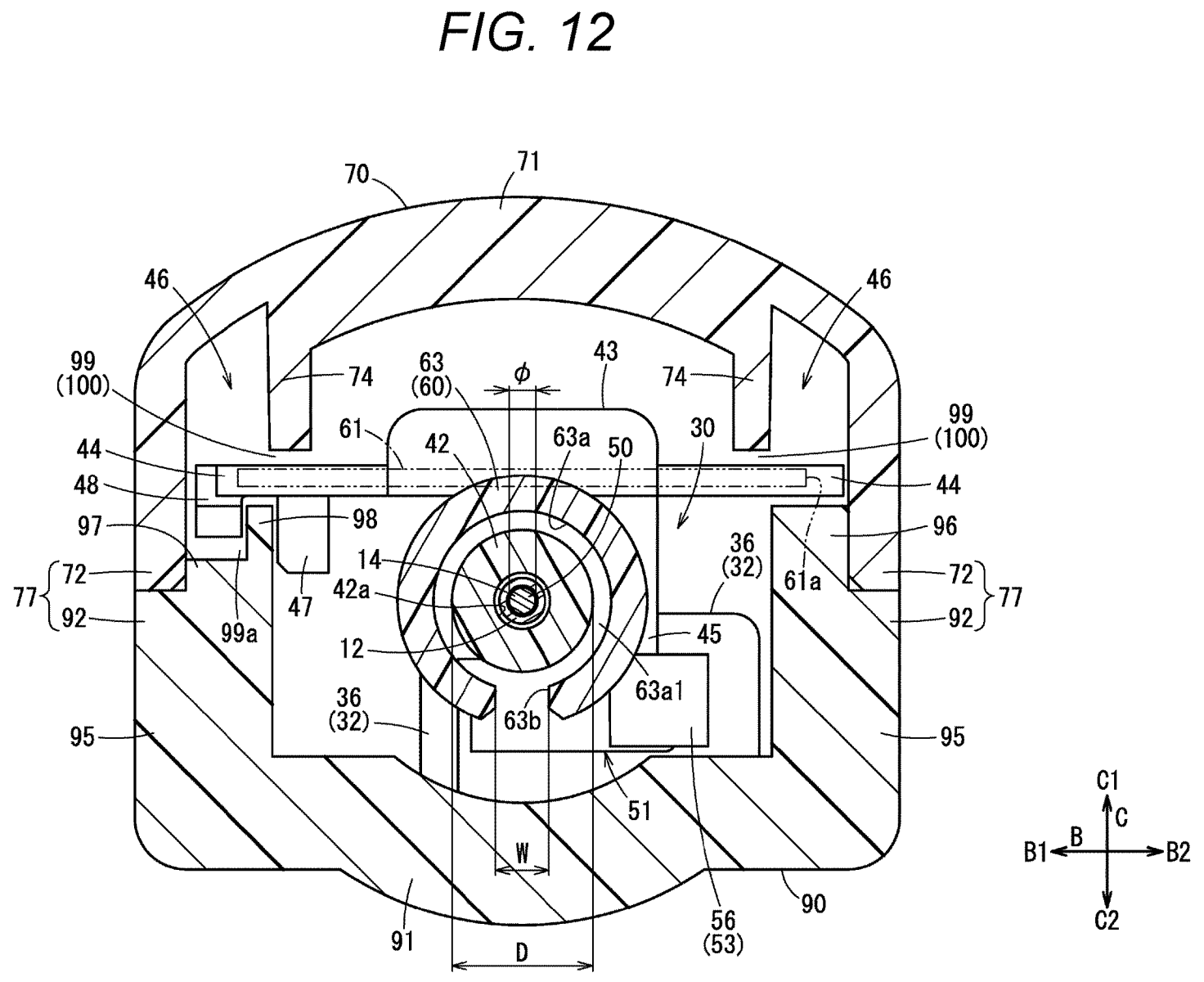

Specifically, a width W of the slit 63b is set to a dimension larger than an outer diameter $\varphi$ of the inner needle 14 having a circular cross section as illustrated in FIGS. 8 and 12. Meanwhile, the width W of the slit 63b is set to a dimension smaller than the outer diameter D of the distal cover portion 42 having a circular cross section. Therefore, the respective dimension of the outer diameter $\varphi$ of the inner needle 14, the outer diameter D of the safety member 40 (the proximal side of the distal cover portion 42), and the width W of the slit 63b have a relationship of $\varphi < W < D$. Note that the width W of the slit 63b may be formed to be slightly smaller than the outer diameter $\varphi$ of the inner needle 14, and the operation member tubular portion 63 may be elastically deformed when the inner needle 14 is caused to pass through the slit 63b.

As illustrated in FIG. 5, the operation member tubular portion 63 is configured to have a length along the axial direction to such an extent to suppress bending of the catheter operation member 60 with respect to the safety member 40. Specifically, an axial length L of the operation member tubular portion 63 is preferably set to ⅓ or more of an axial length of the hub accommodation portion 62 accommodating the catheter hub 20. As a result, the linearity of the catheter operation member 60 and the safety member 40 can be favorably maintained at the time of operating the catheter operation member 60.

Returning to FIG. 1, the grip 18 of the catheter assembly 10 is formed to have an appropriate thickness that can be easily held by the user, and extends by a predetermined length along the arrow A direction. The accommodation space 18a in which the catheter 12, the catheter hub 20, the safety member 40, and the catheter operation member 60 can advance and retract is formed in the grip 18. The accommodation space 18a communicates with a distal opening portion 18b of the grip 18, and can deliver the catheter 12, the catheter hub 20, the safety member 40, and the catheter operation member 60. The grip 18 is configured by assembling an upper grip 70 (first member) and the lower grip 90 (second member) that are dividable in the arrow C direction (direction orthogonal to the longitudinal direction).

Figure 9:
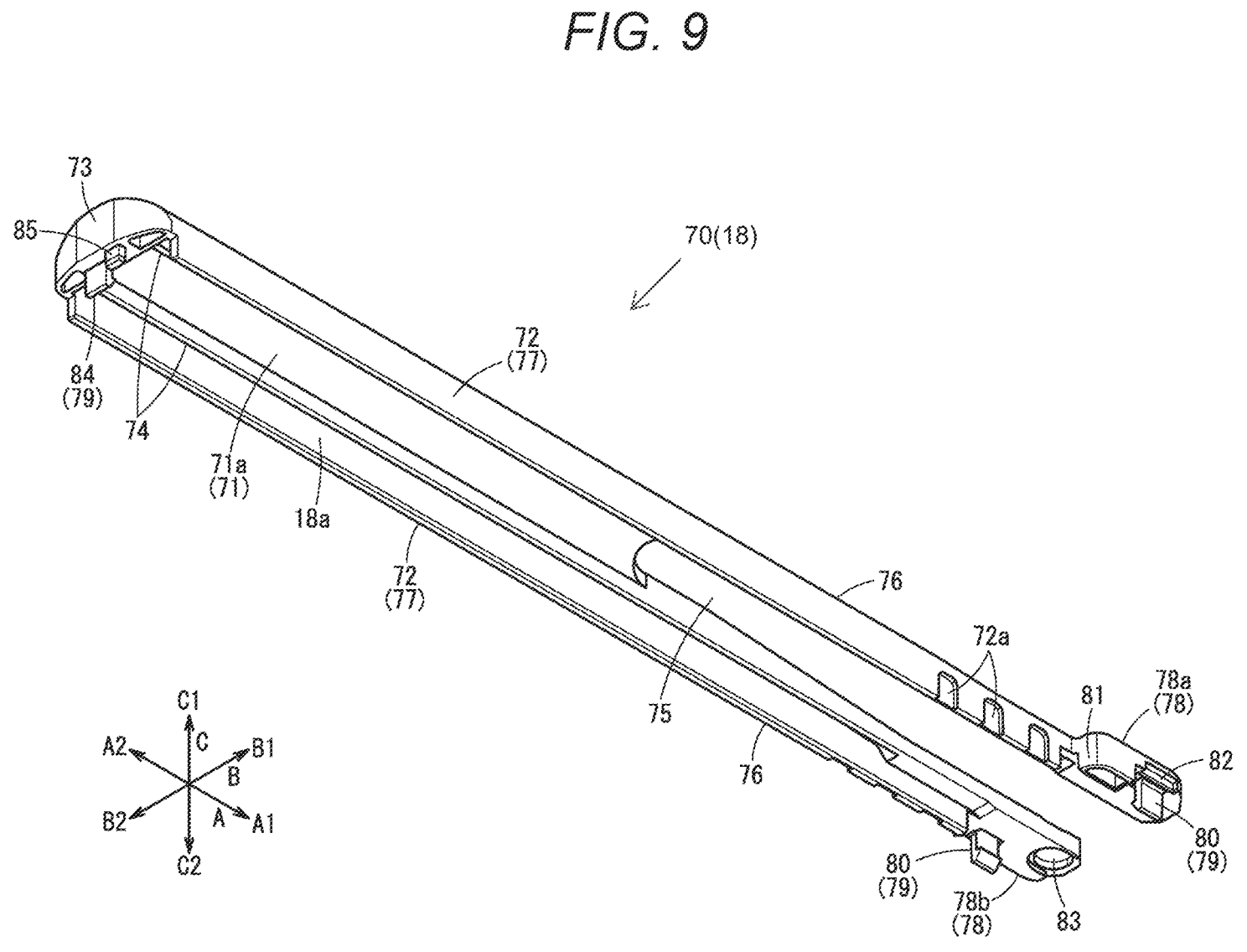

As illustrated in FIGS. 1, 2, and 9, the upper grip 70 has a ceiling wall 71, a pair of upper side walls 72, and an upper rear wall 73, and is formed in a recessed shape (bowl shape) that is opened downward. The ceiling wall 71 has a covering portion 71a whose upper portion is not exposed from an intermediate portion in the arrow A direction to a proximal end. The covering portion 71a is formed in an arc shape in a sectional view. A pair of ridge portions 74 protruding slightly downward from the pair of upper side walls 72 and extending in the arrow A direction is provided on a lower surface (inner side) of the covering portion 71a. The pair of ridge portions 74 is arranged close to an upper surface of the cover body 41 (the pair of protruding portions 44) above the cover body 41, and constitutes a part of the guide mechanism 46 that guides the advancement and retraction of the cover body 41 (see also FIG. 12).

On the other hand, the ceiling wall 71 has a pair of (bifurcated) extending portions 76 by forming an operation member exposure notch 75 at the center in the arrow B direction on the distal side with respect to an intermediate portion. The pair of upper side walls 72 and the pair of ridge portions 74 extend from the proximal end of the covering portion 71a to substantially distal ends of the pair of extending portions 76 (to proximal ends of upper projecting piece portions 78 to be described later) to reinforce the pair of extending portions 76.

In addition, the pair of upper side walls 72 protrudes downward from sides of the ceiling wall 71 to constitute the side walls 77 of the grip 18 together with the lower side wall 92 of the lower grip 90. The upper side wall 72 on the arrow B1 side accommodates the locked protrusion 48 of the cover body 41 inside and does not expose the locked protrusion 48 in the state before puncture. In addition, a plurality of upper recesses 72a that guide gripping of the user are formed on the distal side of each of the upper side walls 72.

The operation member exposure notch 75 of the upper grip 70 is formed between the pair of ridge portions 74 and communicates with the accommodation space 18a. The operation member exposure notch 75 exposes the tab 64 of the catheter operation member 60 so as to be advanced and retracted. The operation member exposure notch 75 is opened at a distal end, and enables advancement of the catheter operation member 60 (tab 64) and detachment from the grip 18.

The pair of extending portions 76 extends such that both sides of the operation member exposure notch 75 gradually decrease from the covering portion 71a toward the arrow A1 side. The upper projecting piece portions 78 each having a substantially flat shape and protruding outward in the width direction from the pair of upper side walls 72 are formed at the distal ends of the pair of extending portions 76. A distal fixing hook 80, which is a part of a fixing mechanism 79 between the upper grip 70 and the lower grip 90, is provided on each of lower surfaces of the pair of upper projecting piece portions 78. Each of the pair of distal fixing hooks 80 includes a claw, which protrudes slightly downward and protrudes inward in the width direction, at a protruding end (lower end).

In addition, a block projection 81 projecting downward to the same extent as the upper side wall 72 is formed on the lower surface of the upper projecting piece portion 78 (hereinafter, referred to as a first upper projecting piece portion 78a) on the arrow B1 side. The block projection 81 partially covers the outer side in the width direction of the safety movement restricting mechanism 49 (a space portion 110) of the lower grip 90 to be described later, and makes the locked protrusion 48 of the safety member 40 having moved to the advanced position not to be substantially exposed. Further, a positioning notch 82 is provided on a side surface of the first upper projecting piece portion 78a on the arrow A1 side with respect to the block projection 81. On the other hand, an upper bearing hole 83 pivotally supporting a lower support member 120 to be described later is provided on the lower surface of the upper projecting piece portion 78 (hereinafter, referred to as a second upper projecting piece portion 78b) on the arrow B2 side. The positioning notch 82 is also provided on a side surface of the second upper projecting piece portion 78b on the arrow B2 side.

The upper rear wall 73 of the upper grip 70 protrudes less than the pair of upper side walls 72 toward the arrow C2 side, and the pair of ridge portions 74 is connected to a distal end surface thereof. A proximal fixing hook 84 constituting a part of the fixing mechanism 79 is provided on a lower surface of the upper rear wall 73, and a fixing projection 85 is formed to protrude at a position near the proximal fixing hook 84 (on the arrow A2 side and the arrow B1 side). The proximal fixing hook 84 includes a claw, which protrudes slightly downward and protrudes toward the arrow A1 side, at a protruding end (lower end).

Figure 10:
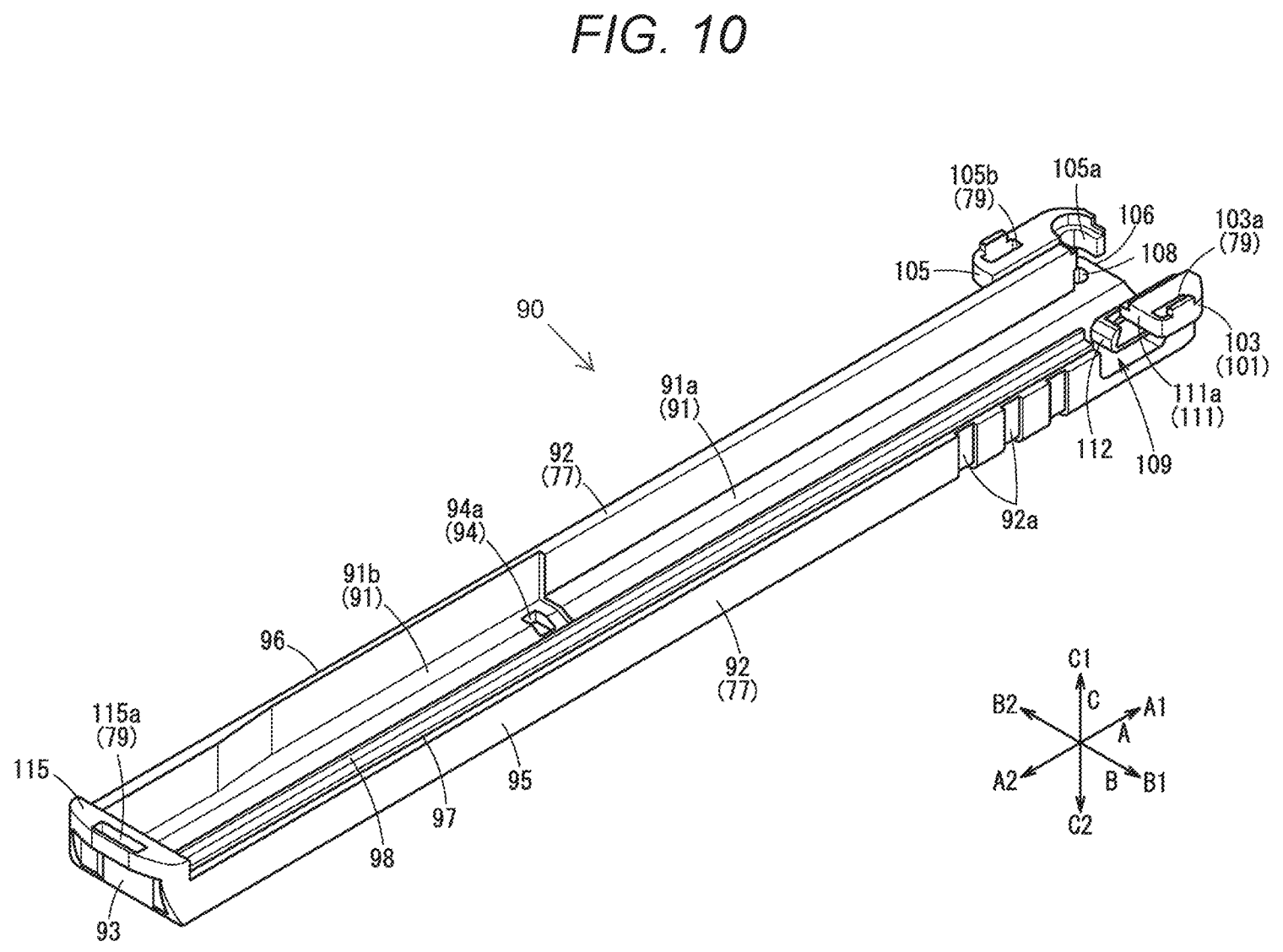

As illustrated in FIGS. 2, 5, and 10, the lower grip 90 has the bottom wall 91, a pair of the lower side walls 92, and a lower rear wall 93, and is formed in a recessed shape (bowl shape) opened upward. A predetermined range on the arrow A1 side of the bottom wall 91 is a guide surface 91a that is formed in an arc shape in which the center in the width direction is recessed downward and guides the advancement and retraction of the catheter hub 20. In addition, a predetermined range on the arrow A2 side of the bottom wall 91 is a mounting target portion 91b which has the same shape as the guide surface 91a but is formed to be lower than the guide surface 91a and on which the inner needle hub 30 is mounted.

Figure 11:
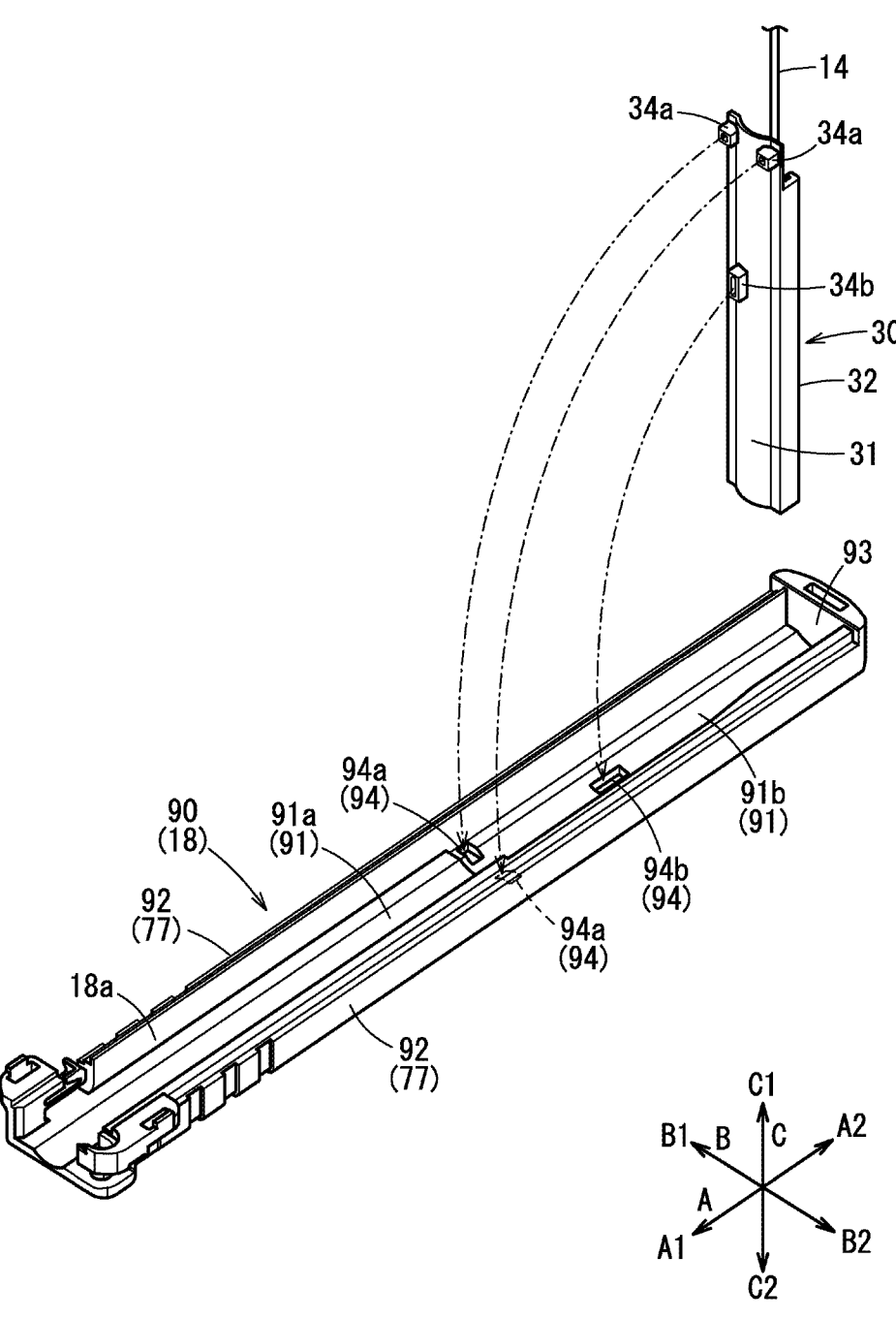
FIG. 11 is an explanatory view for describing fixation of the inner needle hub and the lower grip.

As illustrated in FIG. 11, the mounting target portion 91b is provided with a plurality of (three in the present embodiment) mounting holes 94 to which the fixing protrusions 34 of the inner needle hub 30 can be fitted. Specifically, the plurality of mounting holes 94 include a pair of two distal mounting holes 94a arranged side by side in the width direction on the distal side of the mounting target portion 91b, and an intermediate mounting hole 94b provided at a position spaced apart from the pair of distal mounting holes 94a by a predetermined distance in the proximal direction. The pair of distal mounting holes 94a is formed in a rectangular shape that is slightly long in the arrow B direction, and the intermediate mounting hole 94*b* is formed in a long hole that is long in the arrow A direction.

That is, when the inner needle hub 30 is mounted on the lower grip 90, the inner needle hub 30 is moved toward the bottom wall 91 of the lower grip 90 (simply inserted to the arrow C2 side). As a result, the pair of distal fixing protrusions 34*a* is inserted into the pair of distal mounting holes 94*a*, and the intermediate fixing protrusion 34*b* is inserted into the intermediate mounting hole 94*b*, so that each of the fixing protrusions 34 and each of the mounting holes 94 are firmly fitted to each other.

As illustrated in FIGS. 2, 10, and 12, the pair of lower side walls 92 of the lower grip 90 protrudes upward (to the arrow C1 side) from sides of the bottom wall 91 and extends over the substantially entire portion in the arrow A direction. A plurality of lower recesses 92*a* that are continuous with the upper recesses 72*a* and guide the gripping of the user are formed on the distal side of the lower side walls 92.

The lower side wall 92 on the arrow B2 side has a lower portion configured as a thick wall 95 and has a rail wall 96 that is continuous to the thick wall 95 on an upper portion and the inner side (the arrow B1 side) of the thick wall 95. That is, a step is formed on the upper portion of the lower side wall 92 and on the arrow B2 side, and the upper side wall 72 of the upper grip 70 is arranged in such a step portion so as to be in close contact with a side surface of the rail wall 96 in the assembled state.

The lower side wall 92 on the arrow B1 side has a lower portion configured as the thick wall 95, and an upper portion of the thick wall 95 is configured as a two-step step. Specifically, a projecting wall 97, which is formed to be the lowest on the arrow B1 side and protrudes slightly to the inner side (the arrow B2 side from the central portion in the width direction), is provided at an upper end of the thick wall 95, and the rail wall 98 protruding slightly is provided at the upper end of the projecting wall 97 on the arrow B2 side. A height of the rail wall 98 on the arrow B1 side is the same as a height of the rail wall 96 on the arrow B2 side. The upper side wall 72 of the upper grip 70 is arranged at the step portion constituted by the thick wall 95 and the projecting wall 97 in the assembled state.

The locked protrusion 48 of the cover body 41 is arranged in the step portion constituted by the projecting wall 97 and the rail wall 98 in the assembled state. That is, a locked protrusion guide space 99*a* (a part of the safety guide space 99) in which the locked protrusion 48 is slidable is formed between the upper side wall 72 of the upper grip 70 and the rail wall 98.

The guide mechanism 46 that guides the safety member 40 includes the pair of upper side walls 72 of the upper grip 70, the pair of ridge portions 74, and the pair of rail walls 96 and 98 of the lower grip 90. That is, the safety guide space 99 to guide the protruding portion 44 of the safety member 40 is formed vertically between the pair of ridge portions 74 and the rail walls 96 and 98 in the assembled state of the upper grip 70 and the lower grip 90. The safety member 40 arranges the rail wall 98 on the arrow B1 side of the lower grip 90 in the gap between the guided projection 47 and the locked protrusion 48 in a state in which the guide mechanism 46 has been constructed. As described above, the side edges 61*a* of the operation plate portion 61 of the catheter operation member 60 are arranged on the pair of rail walls 96 and 98 so that the advancement and retraction of the catheter operation member 60 can also be guided (in FIG. 12, the operation plate portion 61 is indicated by a two-dot chain line). In other words, the safety guide space 99 shares an operation member guide space 100 in the present embodiment.

The safety guide space 99 is opened upward in a state in which the upper grip 70 is separated from the lower grip 90, and is closed in a state in which the upper grip 70 is fixed to the lower grip 90. Meanwhile, the pair of side edges 61*a* of the catheter operation member 60 is formed to have a width narrower than a width of the pair of protruding portions 44 of the safety member 40, and is arranged on the pair of rail walls 96 and 98. Therefore, the operation member guide space 100 is set to be narrower than the safety guide space 99 by the lower support member 120 to be described later, is opened at the distal end (distal opening portion 18*b*) of the grip 18, and can deliver the catheter operation member 60.

Figure 13A:
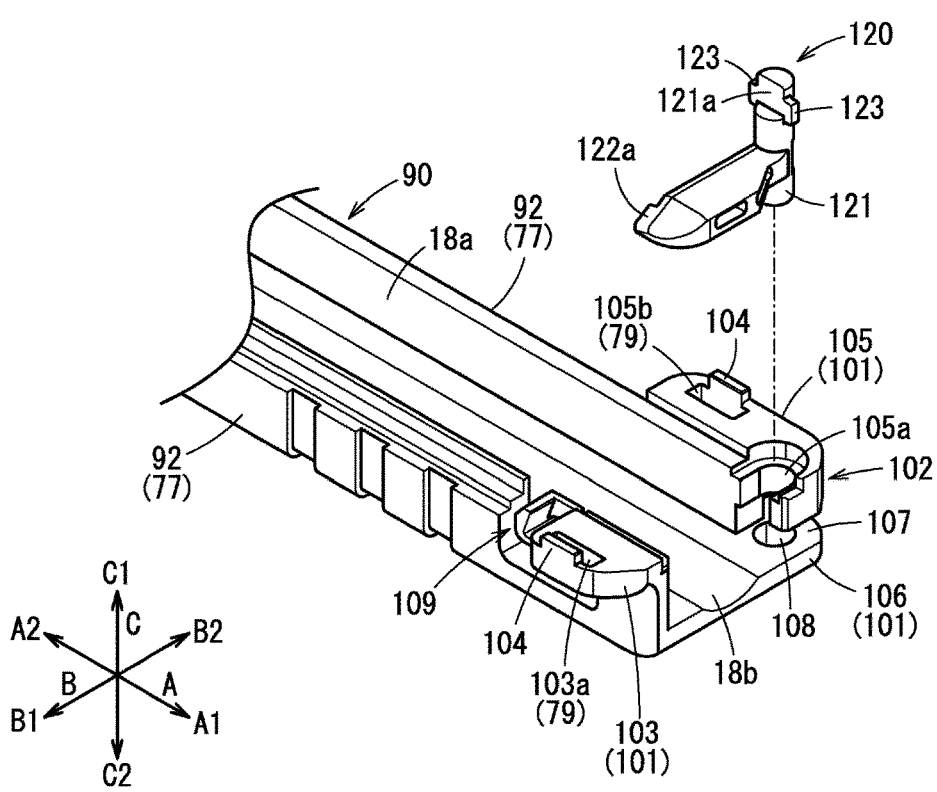
FIG. 13A is a perspective view illustrating a state before assembling of the lower grip and a lower support member.
Figure 13B:
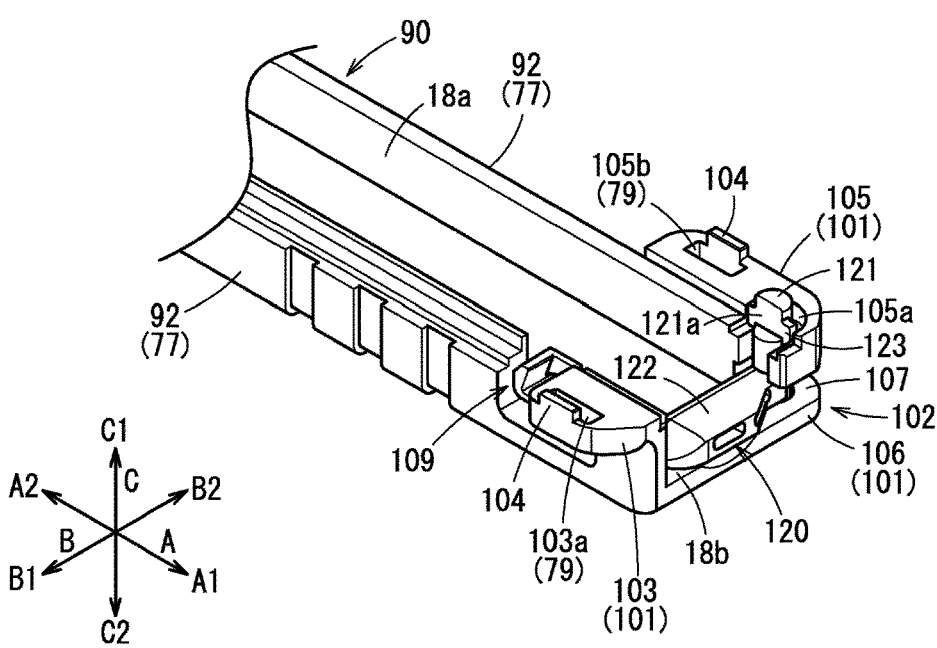
FIG. 13B is a perspective view illustrating a state in which the lower grip and the lower support member are assembled.

As illustrated in FIGS. 13A and 13B, a pair of projecting bodies 101 protruding outward in the width direction from the pair of lower side walls 92 is provided at the distal end of the lower grip 90. The pair of projecting bodies 101 has a sufficient thickness along the arrow C direction, and upper surfaces thereof are located at positions slightly higher than upper ends of the rail walls 96 and 98. The pair of projecting bodies 101 constitutes the fixing mechanism 79 for fixing the upper grip 70 and the lower grip 90 and an arrangement mechanism 102 for arranging the lower support member 120.

The projecting body 101 on the arrow B1 side (hereinafter, referred to as a first projecting body 103) protrudes from the upper portion of the lower side wall 92 to the arrow B1 side. A first fixing hole 103*a*, which is a part of the fixing mechanism 79, is formed to penetrate through the first projecting body 103 in the thickness direction. When the distal fixing hook 80 of the first upper projecting piece portion 78*a* is inserted into the first fixing hole 103*a* at the time of assembly, the claw is caught by a lower end surface of the projecting body 101. In addition, a positioning projection 104 protruding slightly upward is provided on the arrow B1 side of the first projecting body 103, and the positioning projection 104 is inserted into the positioning notch 82 of the first upper projecting piece portion 78*a*.

The projecting body 101 on the arrow B2 side protrudes to the arrow B2 side from the upper and lower sides of the lower side wall 92 (hereinafter, a portion on the arrow C1 side is referred to as a second projecting body upper block 105, and a portion on the arrow C2 side is referred to as a second projecting body lower block 106), and a movement space 107 in which the lower support member 120 is rotatably movable is provided therebetween. A bearing notch 105*a* rotatably supporting the lower support member 120 is provided on the distal side of the second projecting body upper block 105. The bearing notch 105*a* is formed in a U shape that is opened to the arrow B1 side in a plan view, and communicates with the accommodation space 18*a* on the inner side thereof. An upper end of the bearing notch 105*a* is formed in a stepped shape having a larger diameter than a lower portion, and a pair of small projections 123 of the lower support member 120, which will be described later, is arranged in the step portion. In addition, the second projecting body upper block 105 has a second fixing hole 105*b*, which is a part of the fixing mechanism 79, is formed to penetrate therethrough in the thickness direction, on the proximal side, and further has the positioning projection 104, to be inserted into the positioning notch 82 of the second upper projecting piece portion 78*b*, on the arrow B2 side.

The second projecting body lower block 106 is provided in a range facing the distal side of the second projecting body upper block 105 in order to constitute the arrangement mechanism 102 of the lower support member 120. A lower bearing hole 108 that pivotally supports the lower support member 120 is provided on an upper surface of the second projecting body lower block 106.

The lower support member 120 is a component that is rotatably attached by the arrangement mechanism 102 of the grip 18 and supports the catheter 12 (multi-piece tube 11) extending below the catheter operation member 60 from below in the state before puncture. In addition, the lower support member 120 rotates as the wall of the hub accommodation portion 62 comes into contact with the lower support member 120 in the movement of the catheter operation member 60, and can deliver the catheter operation member 60 from the accommodation space 18a.

The lower support member 120 includes a shaft 121 extending in the arrow C direction and a supporting body portion 122 protruding in a direction orthogonal to the axial center of the shaft 121. The shaft 121 has an upper portion provided with a guide plane 121a continuous with the upper end of the rail wall 96 and the pair of small projections 123 having the guide plane 121a. In the state before puncture, the side edge 61a of the catheter operation member 60 is close to the guide plane 121a to restrict the rotation of the lower support member 120.

The supporting body portion 122 is narrow in the vicinity of a coupling portion with the shaft 121 in a plan view, and becomes wider as a distance from the vicinity of the coupling portion increases. An upper surface of the supporting body portion 122 is formed in a flat shape (parallel to the bottom wall 91) from the shaft 121 toward the protruding direction, and is inclined downward at a protruding end. An inclined projection 122a along the upper surface is formed to protrude on the proximal side of the protruding end.

The lower support member 120 configured as described above is inserted along the bearing notch 105a from above the lower grip 90 in a posture in which the supporting body portion 122 faces the arrow B1 side. At this time, the lower support member 120 is smoothly inserted into the bearing notch 105a and the lower bearing hole 108 as the vicinity of the coupling portion of the supporting body portion 122 passes through the opening portion on the accommodation space 18a side of the bearing notch 105a. When the upper grip 70 and the lower grip 90 are mounted, the upper end of the shaft 121 supported by the lower grip 90 is arranged in the upper bearing hole 83 of the upper grip 70.

In the state before puncture, the side edge 61a of the catheter operation member 60 is present on the guide plane 121a, and thus, the supporting body portion 122 is restricted from rotating and stands by to be capable of supporting the catheter 12. As a result, the supporting body portion 122 supports the catheter 12 from below to suppress the deflection of the catheter 12. When the catheter operation member 60 comes out of the grip 18, the lower support member 120 becomes rotatable as the side edge 61a comes out of the guide plane 121a, and allows the catheter operation member 60 and the safety member 40 to be delivered.

Figure 14:
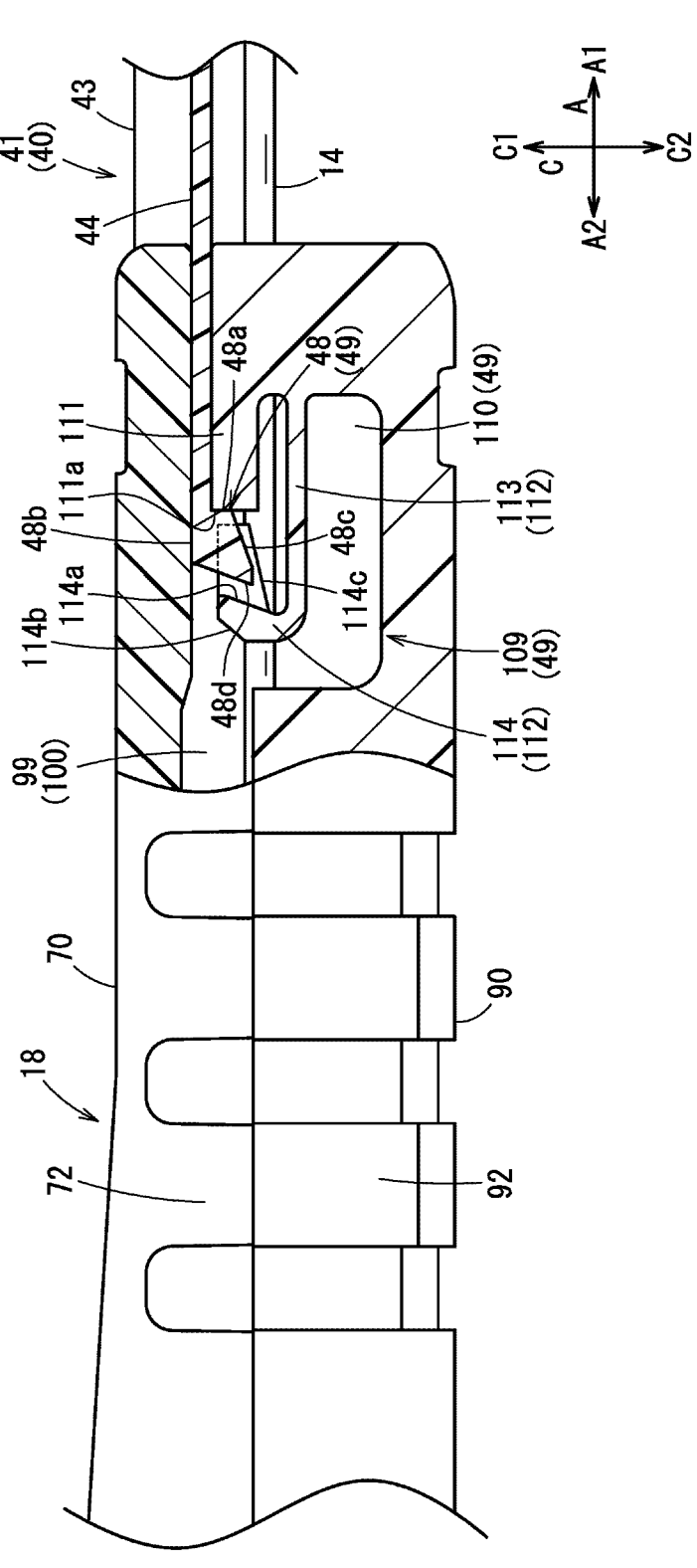
FIG. 14 is a partial side sectional view illustrating a safety movement restricting mechanism that restricts movement of the cover body using the grip.

As illustrated in FIG. 14, the locking portion 109, which is the other of the safety movement restricting mechanisms 49 that restrict the movement of the safety member 40 (cover body 41), is provided on the lower side wall 92 on the arrow B1 side of the lower grip 90. The locking portion 109 includes the space portion 110 obtained by cutting out the lower side wall 92 from the upper side, an advancement restricting portion 111 facing an advancing direction of the locked protrusion 48, and a retraction restricting portion 112 that restricts the retraction of the locked protrusion 48. The space portion 110 communicates with a distal end of the safety guide space 99.

The advancement restricting portion 111 protrudes from the upper side (arrow C1 side) of the space portion 110 to the arrow A2 side and is continuous with the first projecting body 103 formed on the outer side in the width direction. A protruding end of the advancement restricting portion 111 on the arrow A2 side is formed on an advancement restricting surface 111a that restricts the advancement of the locked protrusion 48. The advancement restricting surface 111a is formed in a flat shape along the arrow C direction.

The retraction restricting portion 112 includes an elastic arm portion 113 extending in the space portion 110 toward the arrow A2 side, and a folded portion 114 inclinedly folded back to the arrow A1 side from a protruding end of the elastic arm portion 113 to the arrow C1 side. The elastic arm portion 113 is elastically deformable in the arrow C direction, and is elastically deformed when the locked protrusion 48 in the middle of advancing comes into contact with the folded portion 114, and is elastically restored when the locked protrusion 48 moves to the arrow A1 side.

The folded portion 114 protrudes to the same height position as the upper end of the rail wall 98. The folded portion 114 has a retraction restricting surface 114a extending toward the arrow C1 side to be inclined toward the arrow A1 side on the inner side of folding (the opposite side of the advancement restricting surface 111a). In the locking portion 109, a position between the advancement restricting surface 111a and the retraction restricting surface 114a is set as the advanced position of the locked protrusion 48.

In addition, an upper end on the outer side of the folded portion 114 extends toward the arrow C1 side to be inclined toward the arrow A1 side, thereby forming a guiding surface 114b that facilitates passing-over of the locked protrusion 48. Further, the folded portion 114 is provided with a thin wall 114c protruding from the retraction restricting surface 114a on the arrow B2 side to the arrow A1 side. The thin wall 114c is at the same position in the width direction as the rail wall 98 on the arrow B1 side, and an inner side surface thereof guides the guided projection 47 of the cover body 41 and prevents the locked protrusion 48 from being displaced to the arrow B2 side.

Here, the locked protrusion 48 of the safety member 40 protrudes slightly from the protruding portion 44 to the arrow B1 side, and is formed in a three-dimensional shape having a distal end surface 48a, an upper surface 48b, a lower surface 48c, and a proximal end surface 48d. The distal end surface 48a is formed parallel to the arrow C direction, and the upper surface 48b is formed parallel to the arrow A direction. On the other hand, the lower surface 48c is a surface that is inclined toward the arrow C2 side from a lower end of the distal end surface 48a to the arrow A2 side, and is guided by the guiding surface 114b of the folded portion 114 when the locked protrusion 48 passes over the folded portion 114. The proximal end surface 48d is inclined toward the arrow A2 side from the upper surface 48b to the arrow C2 side, and faces the retraction restricting surface 114a in the same inclination direction when the locked protrusion 48 moves to the advanced position. As a result, when a retraction force is applied to the safety member 40, the proximal end surface 48d of the locked protrusion 48 and the retraction restricting surface 114a are positively caught by each other to restrict the retraction of the safety member 40.

Returning to FIG. 10, the lower rear wall 93 of the lower grip 90 has a proximal end flange 115 protruding toward the arrow C1 side and protruding toward the arrow A2 side from the rail walls 96 and 98. In the proximal end flange 115, a third fixing hole 115a is formed to penetrate along its thickness direction. The third fixing hole 115a is formed to be long in the arrow B direction, and enables the proximal fixing hook 84 and the fixing projection 85 to be inserted therein together.

The catheter assembly 10 according to the present embodiment is basically configured as described above, and assembling of the catheter assembly 10 will be described hereinafter.

Figure 15:
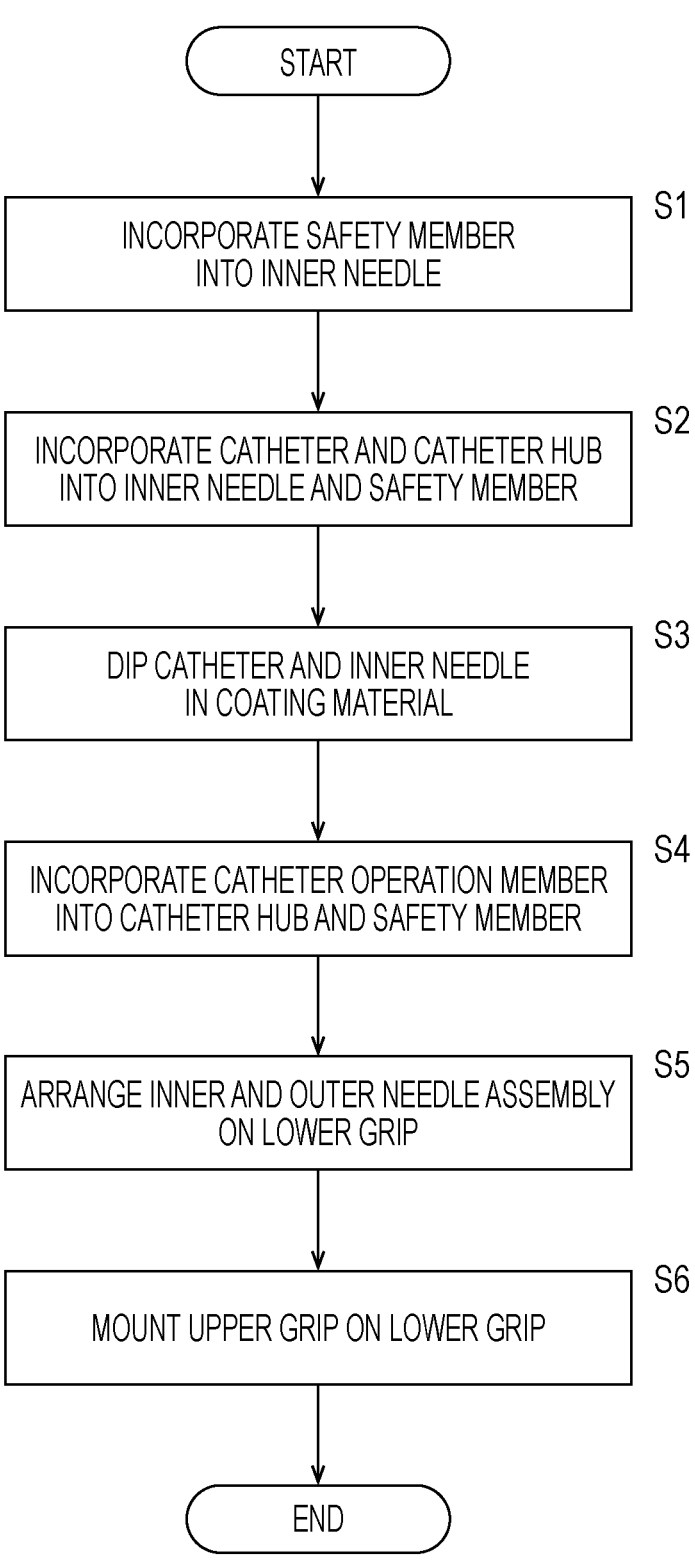
FIG. 15 is a flowchart illustrating a procedure at the time of assembling the catheter assembly.

The catheter assembly 10 assembles the respective members according to a procedure illustrated in FIG. 15. Schematically, after the inner and outer needle assembly 16 is assembled first, the inner and outer needle assembly 16 is arranged on the lower grip 90, and the upper grip 70 is mounted onto the inner and outer needle assembly 16 and the lower grip 90.

Figure 16:
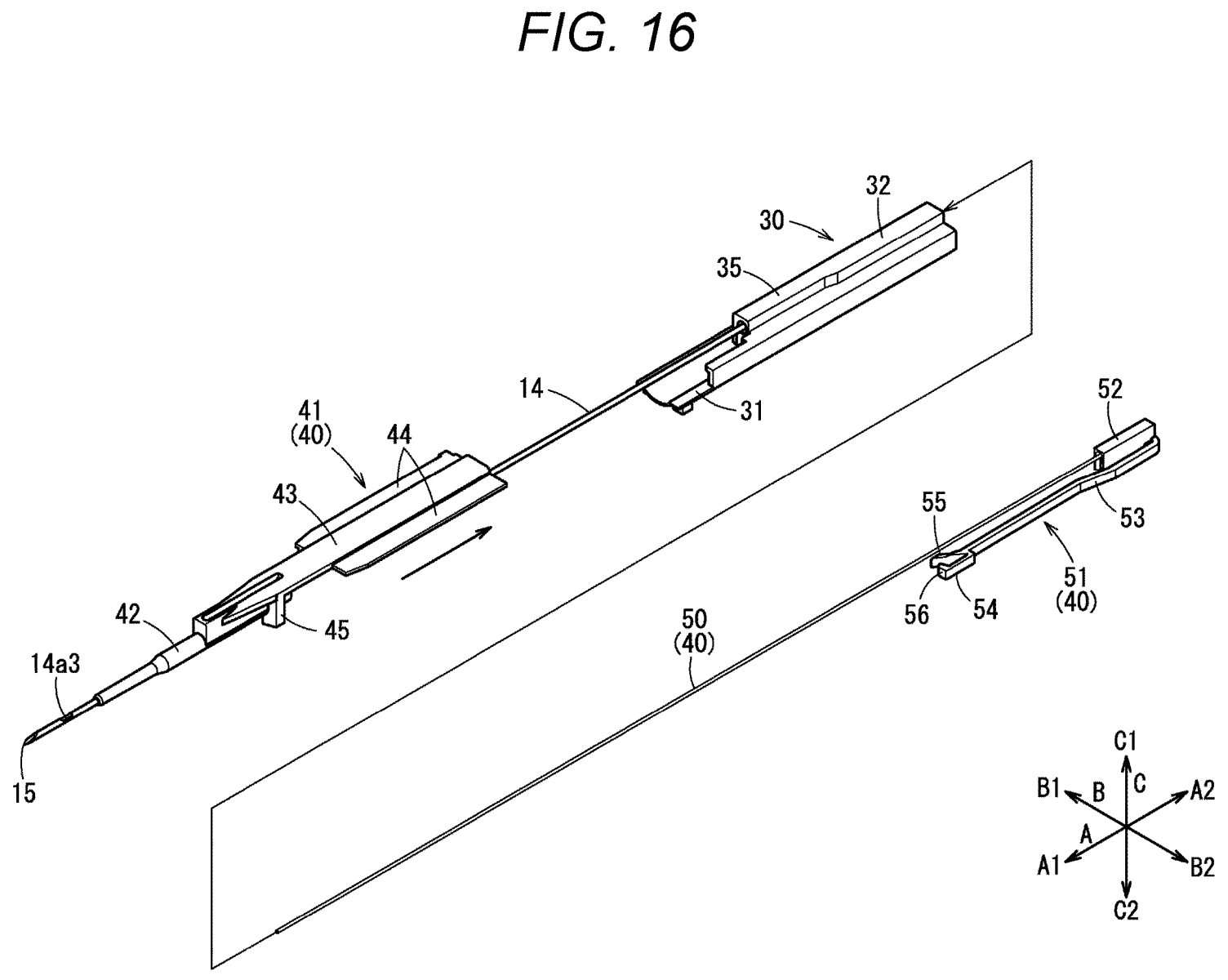

When the inner and outer needle assembly 16 is assembled, first, a process of incorporating the safety member 40 into the inner needle 14 is performed (step S1). In this case, a component in which the inner needle 14 and the inner needle hub 30 have been fixed in advance, a component in which the blunt needle 50 and the blunt needle hub 51 have been fixed in advance, and the cover body 41 are prepared as illustrated in FIG. 16. Then, the distal end of the blunt needle 50 is inserted from the proximal end of the inner needle hub 30, and the blunt needle 50 is advanced along the hollow portion 14a of the inner needle 14. The arm portion 53 of the blunt needle hub 51 is guided to the distal side of the holding frame portion 32 through the space in the holding frame portion 32 of the inner needle hub 30, and the blunt needle holding portion 52 of the blunt needle hub 51 is arranged at a position facing a proximal end of the tubular portion 35 in the holding frame portion 32.

Then, the distal end of the inner needle 14 is inserted from the proximal end of the distal cover portion 42 (protective space 42a) of the cover body 41. Because the distal cover portion 42 has a tubular shape that is thick on the proximal side and the protective space 42a is also wide, the needle tip 15 of the inner needle 14 can be easily inserted. When the cover body 41 is moved in the proximal direction along the inner needle 14 and the engagement projection 45 of the cover body 41 reaches the distal end of the arm portion 53 of the blunt needle hub 51 that has passed through the inner needle hub 30, the engagement projection 45 and the engagement portion 54 engage with each other to be integrated as the safety member 40. That is, at this stage, the inner needle 14 is exposed from the distal end of the safety member 40, thereby forming a safety-retaining assembly 130.

Figure 17:
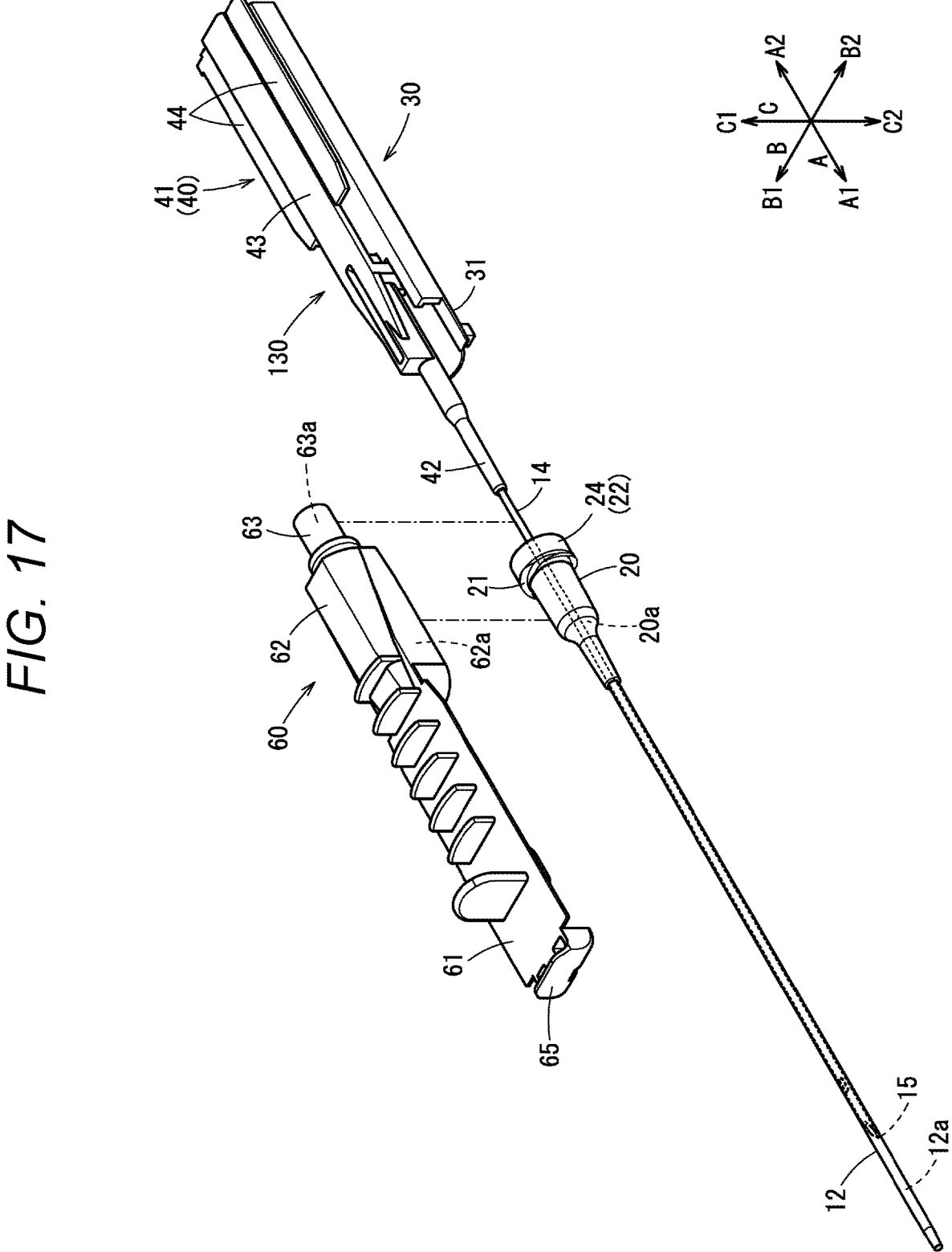
FIG. 17 is a second explanatory view illustrating the assembly procedure of the catheter assembly.

Next, a process of incorporating a component (indwelling body) in which the catheter 12 and the catheter hub 20 (including the valve member 22) have been fixed in advance into the safety-retaining assembly 130 including the inner needle 14 and the safety member 40 is performed (step S2). As illustrated in FIG. 17, the distal end of the inner needle 14 is inserted into the valve hole 25 of the valve member 22 from the proximal side in a state in which the valve member 22 has been inserted into the catheter hub 20. At this time, the valve hole 25 is easily opened since the distal cover portion 42 of the cover body 41 is not yet inserted into the valve member 22.

Therefore, the valve member 22 smoothly moves on the outer peripheral surface of the inner needle 14 while suppressing piercing of the inner needle 14.

Then, the catheter hub 20 is temporarily mounted onto an outer peripheral surface of the distal cover portion 42 by continuing to move the catheter hub 20 in the axial direction (proximal direction). In this state, the catheter hub 20 and the distal cover portion 42 are fitted to each other through the valve member 22. Then, the multi-piece tube 11 in which the needle tip 15 of the inner needle 14 protrudes from the distal end of the catheter 12 is formed at the distal end of the catheter hub 20.

In the above-described formation state of the multi-piece tube 11, a process of immersing (dipping) the catheter 12 and the inner needle 14 in the coating material 13 is performed as illustrated in FIG. 15 (step S3). In this dipping, the coating material 13 is stored in a storage tank (not illustrated), and the multi-piece tube 11 in the state of having the safety-retaining assembly 130 at its proximal end enters a stored liquid from above to below with its distal end facing downward. Then, the catheter hub 20 waits for a certain period of time at a position where the catheter hub 20 is not immersed, and then, the multi-piece tube 11 is pulled upward. As a result, the coating material 13 is applied to the surface of the catheter 12 and the needle tip 15. At the time of dipping, the coating material 13 is not applied to the catheter operation member 60 since the catheter operation member 60 is not yet mounted.

After the formation of the coating material 13, a process of incorporating the catheter operation member 60 is performed (step S4). In this step, the catheter hub 20 and the safety member 40 fitted to each other for the dipping are separated. That is, the catheter hub 20 is relatively moved in the axial direction (distal direction) with respect to the safety member 40 (safety-retaining assembly 130) as illustrated in FIG. 17. As a result, the inner needle 14 is exposed at the proximal end of the valve member 22 of the catheter hub 20 and at the distal end of the distal cover portion 42.

The catheter operation member 60 is mounted from the side in a state in which the inner needle 14 is exposed between the proximal end of the valve member 22 and the distal end of the safety member 40. Here, since the width W of the slit 63b formed in the operation member tubular portion 63 of the catheter operation member 60 is larger than the outer diameter φ of the inner needle 14, the inner needle 14 can be smoothly inserted into the insertion space 63a of the operation member tubular portion 63 through the slit 63b. Because the hub accommodation portion 62 of the catheter operation member 60 is opened on the lower side, the catheter hub 20 (including the valve member 22) can be easily inserted into the accommodation chamber 62a with the inner needle 14 inserted therein.

Then, the catheter hub 20 and the catheter operation member 60 are moved in the proximal direction in a state in which the catheter hub 20 (including the valve member 22) is accommodated in the catheter operation member 60. As a result, the distal end of the safety member 40 is inserted again into the valve hole 25 of the valve member 22. At a stage in which the proximal end of the operation member tubular portion 63 of the catheter operation member 60 reaches the distal end of the distal cover portion 42 of the safety member 40 and the distal end of the coupling portion 43a of the proximal extending portion 43, the safety member 40 is strongly fitted to the valve member 22. As a result, the inner and outer needle assembly 16 in which the catheter 12, the catheter hub 20, the inner needle 14, the inner needle hub 30, the safety member 40, and the catheter operation member 60 are assembled is constructed.

Figure 18:
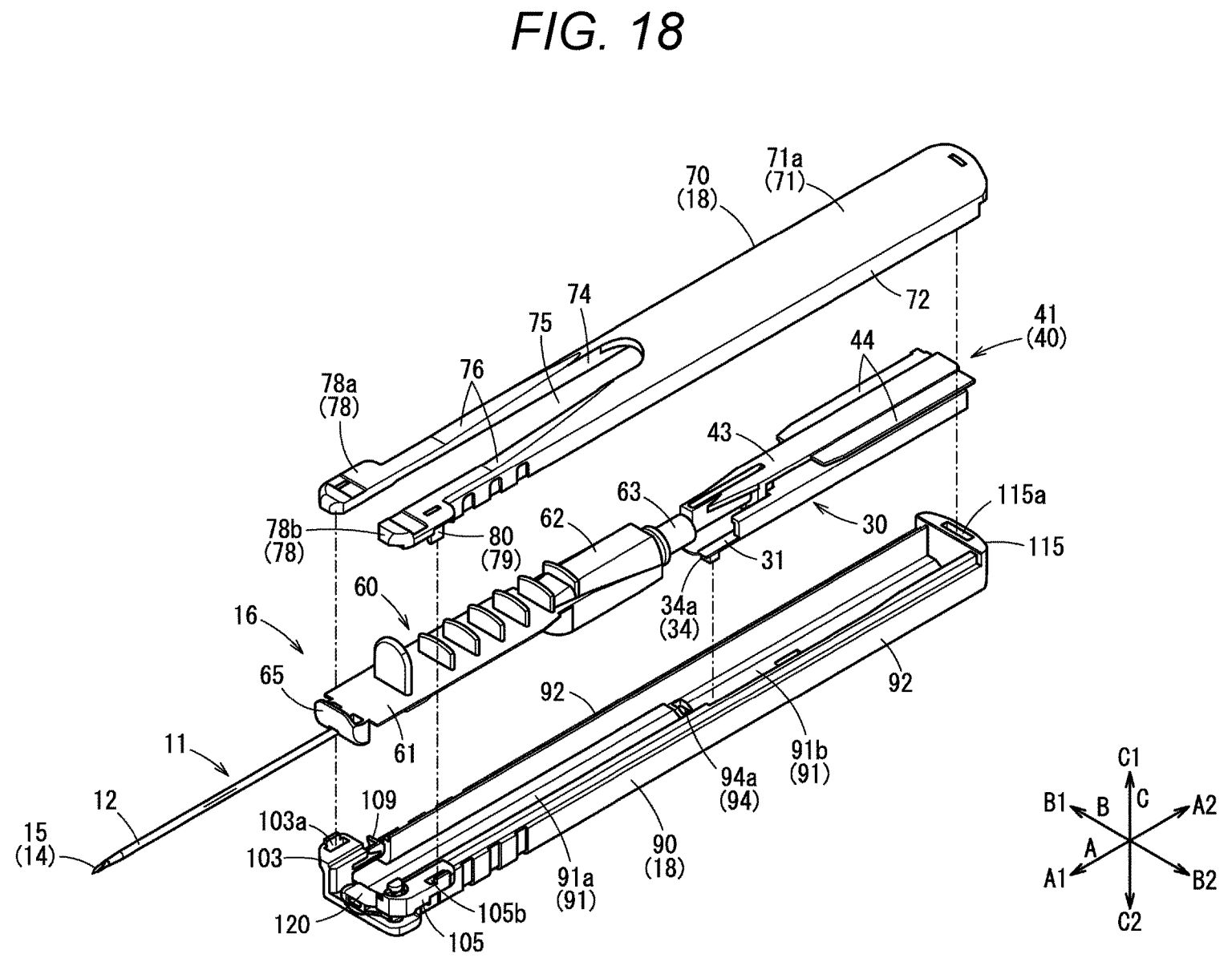

Thereafter, during the assembling, a process of arranging the inner and outer needle assembly 16 assembled in advance on the lower grip 90 is performed (step S5). At this time, the lower grip 90 is set to a state of mounting the lower support member 120 by the above-described assembling method (see FIGS. 13A and 13B). As illustrated in FIG. 18, during the assembling, the inner and outer needle assembly 16 are inserted from the opening portion on the upper side of the lower grip 90 toward the lower side (arrow C2 side), and the plurality of fixing protrusion 34 of the inner needle hub 30 are inserted and fitted into the plurality of mounting holes 94 of the lower grip 90, respectively (see also FIG. 11). As a result, the inner and outer needle assembly 16 is engaged with the lower grip 90.

Here, the safety guide space 99 (space portion 110) formed between the upper grip 70 and the lower grip 90 and the operation member guide space 100 are opened in a state in which the upper grip 70 is separated from the lower grip 90. Therefore, the safety member 40 and the catheter operation member 60 can be easily arranged by inserting the inner and outer needle assembly 16 toward the arrow C2 side with respect to the lower grip 90.

Finally, during the assembling, a process of mounting the upper grip 70 onto the lower grip 90 that has been engaged with the inner and outer needle assembly 16 is performed (step S6). That is, the upper grip 70 is brought closer to the lower grip 90 from the upper side toward the lower side (arrow C2 side), and the distal fixing hooks 80 of the first and second upper projecting piece portions 78a and 78b of the upper grip 70 are inserted into the first and second fixing holes 103a and 105b of the lower grip 90 to be caught by the first projecting body 103 and the second projecting body upper block 105. The proximal fixing hook 84 and the fixing projection 85 of the upper grip 70 are inserted into the third fixing hole 115a of the lower grip 90, and the proximal fixing hook 84 is caught by the proximal end flange 115. As described above, the upper grip 70 and the lower grip 90 are firmly integrated as the grip 18 by mutually fixing the two points sandwiching the catheter operation member 60 at the distal end and one point at the proximal end.

The assembling of the catheter assembly 10 is completed by fixing the upper grip 70 and the lower grip 90 and forms the state before puncture. In this state, the safety guide space 99 (space portion 110) in which the pair of protruding portions 44 (locked protrusions 48) of the safety member 40 is arranged is closed in the arrow A direction of the upper grip 70 and the lower grip 90 to prevent detachment of the pair of protruding portions 44. Since the inner needle hub 30 is fixed to the grip 18 in the inner and outer needle assembly 16, the inner needle 14 is not movable, and the catheter 12, the catheter hub 20, the safety member 40, and the catheter operation member 60 can advance and retract relative to the inner needle 14.

Incidentally, the present invention is not limited to the above-described embodiment, and various modifications can be made in accordance with a gist of the invention. For example, the attachment mechanism 33 that fixes the inner needle hub 30 and the lower grip 90 is not limited to the above, and can adopt various configurations (an adhesion structure, a fixing structure using a hook, and the like). In addition, the fixing mechanism 79 for fixing the upper grip 70 and the lower grip 90 is not limited to the above, and may adopt various configurations (an adhesion structure, a fitting structure, and the like).

Modification

Figure 19A:
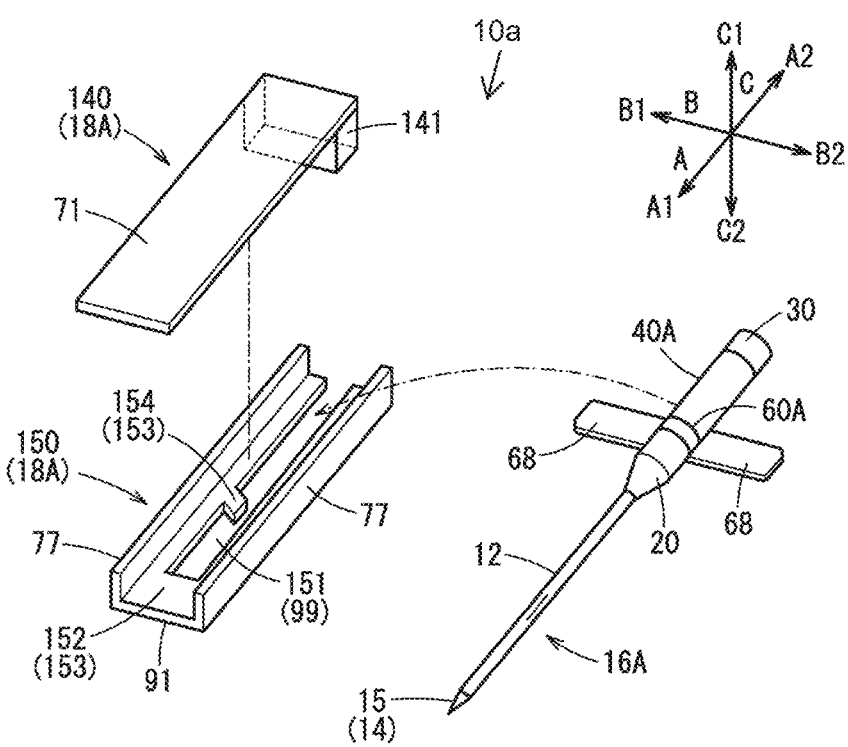
FIG. 19A is a perspective view schematically illustrating an exploded state of a catheter assembly according to a modification.
Figure 19B:
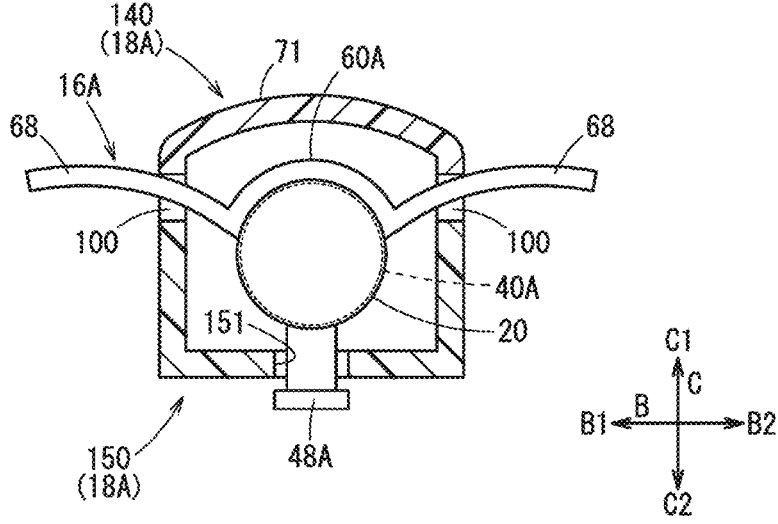
FIG. 19B is a sectional view in a direction orthogonal to the longitudinal direction of the catheter assembly of FIG. 19A.

A catheter assembly 10A according to a modification illustrated in FIGS. 19A and 19B is different from the above-described catheter assembly 10 in that a structure for guiding and restricting movement of a safety member 40A is provided in a different direction from a point where an operation portion of a catheter operation member 60A is arranged. Incidentally, an element having the same configuration or the same function as that in the above-described embodiment will be denoted by the same reference sign, and the detailed description thereof will be omitted in the following description.

Specifically, a grip 18A of the catheter assembly 10A can be divided into an upper grip 140 and a lower grip 150. The upper grip 140 includes the ceiling wall 71 and a rear block body 141 on the arrow A2 side, but does not include a side wall.

The lower grip 150 includes the bottom wall 91 and the pair of side walls 77, but does not include a rear wall on the arrow A2 side. The bottom wall 91 of the lower grip 150 is provided with a long guide hole 151 (the safety guide space 99) that guides a locked protrusion 48A of the safety member 40A. The long guide hole 151 has a distal end to be closed by the lower grip 150 alone and a proximal end being opened. The opening portion of the proximal end of the long guide hole 151 is closed by the rear block body 141 as the upper grip 140 is mounted onto the lower grip 150.

In an assembled state of the upper grip 140 and the lower grip 150, the operation member guide space 100 is formed between the ceiling wall 71 of the upper grip 140 and each of the side walls 77 of the lower grip 150. A pair of wings 68 (operation portions) of the catheter operation member 60A is arranged in a pair of the operation member guide spaces 100, respectively. The catheter operation member 60A is engaged with the catheter hub 20 or the safety member 40A, and can advance and retract the catheter 12, the catheter hub 20, and the safety member 40A based on the operation of the pair of wings 68 performed by a user.

An inner and outer needle assembly 16A of the catheter assembly 10A is configured by assembling the catheter 12, the catheter hub 20, the inner needle 14, the inner needle hub 30, the safety member 40A, and the catheter operation member 60A. The inner needle hub 30 fixes a proximal end of the inner needle 14 and is fixed to a mounting portion (not illustrated) on the proximal side of the lower grip 150 constituting the attachment mechanism 33. The safety member 40A includes the locked protrusion 48A at a proximal end of a tubular portion through which the inner needle 14 is inserted. The locked protrusion 48A protrudes by a predetermined length toward the arrow C2 side, and a protruding end thereof is configured to be wider than the long guide hole 151. Therefore, the locked protrusion 48A (safety member 40A) is prevented from coming out of the long guide hole 151 in the assembled state.

The long guide hole 151 extends along the longitudinal direction (arrow A direction) of the lower grip 150, and a closed portion 152 at the distal end thereof reaches the vicinity of the distal end of the lower grip 150. A locking portion 153 (a part of the safety movement restricting mechanism 49) that restricts the movement of the locked protrusion 48A (safety member 40A) at an advanced position at which the locked protrusion 48A has advanced is provided slightly closer to the proximal side than the closed portion 152 of the long guide hole 151.

The locking portion 153 includes the closed portion 152 at the distal end of the long guide hole 151 and a convex portion 154 (folded piece portion) that narrows the long guide hole 151 inward in the width direction. The convex portion 154 is elastically deformed when the locked protrusion 48A advances to the arrow A1 side to move the locked protrusion 48A to the advanced position, and restricts the locked protrusion 48A that has been moved to the advanced position from retracting to the arrow A2 side. As a result, the movement of the safety member 40A is restricted in a state of being exposed from the grip 18A together with the catheter hub 20 and covering the needle tip 15 of the inner needle 14 at the advanced position, and it is possible to satisfactorily inhibit erroneous puncture of the inner needle 14.

In the above-described catheter assembly 10A, the pair of wings 68 of the catheter operation member 60A is arranged at a boundary (the operation member guide space 100) between the upper grip 140 and the lower grip 150 and is movable. Thus, the delivery of the catheter operation member 60A from the grip 18A becomes easy. Since the safety movement restricting mechanism 49 of the safety member 40A is not shared as the operation member guide space 100, it is possible to simplify the configuration of the distal end of the grip 18A and to firmly restrict the advancement and retraction of the safety member 40A at the advanced position.

Technical ideas and effects that can be grasped from the above-described embodiment are described as follows.

One aspect of the present invention provides a catheter assembly 10 or 10A including: an inner and outer needle assembly 16 or 16A in which a catheter 12, a catheter hub 20 holding the catheter 12, an inner needle 14 inserted through the catheter 12, an inner needle hub 30 holding the inner needle 14, and a safety member 40 or 40A that is movable together with the catheter hub 20 and advances beyond a needle tip 15 of the inner needle 14 stuck into a treatment target to activate an erroneous puncture inhibition function of the inner needle 14 are assembled; and a grip 18 or 18A which accommodates the inner and outer needle assembly 16 or 16A. The grip 18 or 18A is configured to accommodate at least a part of the safety member 40 or 40A from before puncture of the inner needle 14 to activation of the erroneous puncture inhibition function, and includes a first member (upper grip 70 or 140) and a second member (lower grip 90 or 150) that are dividable in a direction orthogonal to a longitudinal direction of the grip (18 or 18A). The second member is capable of fixing the inner needle hub 30 from a separated state of the first member as the inner and outer needle assembly 16 or 16A is arranged along an assembling direction of the first member, and makes the safety member 40 or 40A undetachable as the first member is assembled after the arrangement of the inner and outer needle assembly 16 or 16A.

Since the catheter assembly 10 or 10A has a configuration in which a part of the safety member 40 or 40A is accommodated in the grip 18 or 18A (in other words, the safety member 40 or 40A does not come out of the grip 18 or 18A) from before puncture to after puncture, it is possible to more reliably inhibit the erroneous puncture of the inner needle 14. Since the inner and outer needle assembly 16 or 16A is arranged in the second member (lower grip 90 or 150) along the assembling direction of the first member (upper grip 70 or 140) in the catheter assembly 10 or 10A, the assembling distance is shortened, the assembling is simplified, and the manufacturing time is greatly shortened. In addition, the possibility of damage to the inner needle 14 can be reduced as compared with insertion along the extending direction of the inner needle 14. Then, the safety member 40 or 40A can be easily undetachable with the assembling of the first member and the second member.

In addition, the safety member 40 and the grip 18 include the safety movement restricting mechanism 49 that defines the advanced position when the safety member 40 advances together with the catheter hub 20 and restricts the movement of the safety member 40 at the advanced position. As a result, the catheter assembly 10 can make the safety member 40 undetachable from the grip 18 by the safety movement restricting mechanism 49, and can more reliably inhibit the erroneous puncture of the inner needle 14.

In addition, the safety movement restricting mechanism 49 includes a locking portion 109 provided in the second member (lower grip 90 or 150) and a locked protrusion 48 provided in the safety member 40 and is locked to the locking portion 109. In this manner, the locked protrusion 48 of the safety member 40 is locked by the locking portion 109 provided in the second member, and thus, the catheter assembly 10 can easily restrict the movement of the safety member 40.

In addition, the locking portion 109 includes: an advancement restricting portion 111 that faces the locked protrusion 48 at the advanced position and restricts the advancement of the locked protrusion 48; and a retraction restricting portion 112 that is elastically deformed by coming into contact with the locked protrusion 48 as the safety member 40 advances, and is elastically restored to restrict the retraction of the locked protrusion 48 after passing over the locked protrusion 48. As a result, the locking portion 109 can satisfactorily restrict the movement of both the advancement and the retraction of the safety member 40.

In addition, the safety member 40 includes a protruding portion 44 that protrudes in a direction different from an advancing direction. A safety guide space 99 that guides the protruding portion 44 is provided at a boundary between the first member (upper grip 70) and the second member (lower grip 90). The safety guide space 99 is opened in a state in which the first member is separated from the second member to enable insertion of the protruding portion 44, and is closed in a state in which the first member and the second member are assembled to prevent detachment of the protruding portion 44. As a result, the catheter assembly 10 can simplify the assembling of the safety member 40 into the safety guide space 99 of the grip 18, and reliably prevent the safety member 40 from falling off in the state of being assembled with the grip 18.

In addition, the inner and outer needle assembly 16 or 16A includes a catheter operation member 60 or 60A configured for a user to operate movement of the catheter 12 and the catheter hub 20. An operation member guide space 100 that guides a part of the catheter operation member 60 or 60A is provided at a boundary between the first member (upper grip 70 or 140) and the second member (lower grip 90 or 150). The operation member guide space 100 is opened in a state in which the first member is separated from the second member to enable insertion of the part of the catheter operation member 60 or 60A. As a result, the catheter assembly 10 or 10A can simplify the assembling of the catheter operation member 60 or 60A into the operation member guide space 100 of the grip 18 or 18A.

In addition, the first member (upper grip 70) has an operation member exposure notch 75 that exposes the catheter operation member 60 from one end toward another end in the longitudinal direction, and the first member and the second member (lower grip 90) include a pair of fixing mechanisms 79 configured to be fixed to each other at one end in the longitudinal direction on an outer side of the operation member exposure notch 75 in a width direction, and at another end in the longitudinal direction. As a result, the grip 18 is firmly fixed at the distal ends and the proximal ends of the first member and the second member, and rattling or the like of the inner and outer needle assembly 16 in the grip 18 can be suppressed.

In addition, the catheter operation member 60A includes a wing 68 protruding from the operation member guide space 100, and the wing 68 is removable from the operation member guide space 100 at one end in the longitudinal direction in a state in which the first member (upper grip 140) and the second member (lower grip 150) are assembled. As a result, the grip 18A can stably transmit an operating force of the user to the catheter operation member 60A to move the catheter 12 and the catheter hub 20, and further, can smoothly deliver the catheter operation member 60A from one end in the longitudinal direction.

In addition, the grip 18 includes a lower support member 120 that supports a lower portion of the catheter 12 when puncture is performed with the catheter 12 and the inner needle 14. The second member (lower grip 90) is provided with an arrangement mechanism 102 that rotatably and pivotally supports a shaft 121 of the lower support member 120. The arrangement mechanism 102 enables insertion of the lower support member 120 by being opened in the assembling direction of the first member (upper grip 70) in a state in which the first member is separated from the second member in an axial direction of the shaft 121, and prevents detachment of the shaft 121 in a state in which the first member and the second member are assembled. As a result, the catheter assembly 10 can satisfactorily make the lower support member 120 undetachable in the assembled state.

In addition, the lower support member 120 has a supporting body portion 122 that protrudes from the shaft 121 to a point where the catheter 12 extends and is capable of coming into contact with the catheter 12, and the second member has a bearing notch 105a that is capable of passing through the supporting body portion 122 when the lower support member 120 is arranged in the arrangement mechanism 102. As a result, the catheter assembly 10 can easily incorporate the lower support member 120 having the supporting body portion 122.

What is claimed is:

1. A catheter assembly comprising:
   a needle assembly extending in a longitudinal direction and comprising:
   a catheter hub holding a catheter,
   an inner needle inserted through the catheter and configured to be punctured into a treatment target,
   an inner needle hub holding the inner needle, and
   a safety member that is movable together with the catheter hub and configured to advance beyond a needle tip of the inner needle, wherein the safety member comprises:
      a proximal extending portion extending in the longitudinal direction, and
      a protruding portion that protrudes from the proximal extending portion in a direction different from the longitudinal direction, wherein the protruding portion is thinner than the proximal extending portion in a direction orthogonal to the longitudinal direction; and
   a grip that accommodates the needle assembly, wherein the grip is configured to accommodate at least a part of the safety member before puncture of the inner needle and until the safety member advances beyond the needle tip, and comprises a first member and a second member that are separable from one another in the direction orthogonal to a longitudinal direction of the grip, wherein:
   a safety guide space is located between the first member and the second member in the direction orthogonal to the longitudinal direction, and a part of the protruding portion is located in the safety guide space.

2. The catheter assembly according to claim 1, wherein:
the safety member and the grip comprise safety movement restricting mechanisms configured to restrict movement of the safety member when the safety member is in an advanced position in which the safety member has advanced together with the catheter hub.

3. The catheter assembly according to claim 2, wherein:
the safety movement restricting mechanisms comprise:
   a locking portion that is provided in the second member, and
   a locked protrusion that is provided in the safety member and is configured to be locked with the locking portion.

4. The catheter assembly according to claim 3, wherein:
the locking portion comprises:
   an advancement restricting portion that faces the locked protrusion and restricts advancement of the locked protrusion when the safety member is in the advanced position, and
   a retraction restricting portion that is elastically deformed by coming into contact with the locked protrusion as the safety member advances, and is elastically restored to restrict retraction of the locked protrusion after passing over the locked protrusion.

5. The catheter assembly according to claim 1, wherein:
the safety guide space is opened in a state in which the first member is separated from the second member to enable insertion of the protruding portion, and is closed in a state in which the first member and the second member are assembled to prevent detachment of the protruding portion.

6. The catheter assembly according to claim 1, wherein:
the needle assembly comprises a catheter operation member configured for a user to operate movement of the catheter and the catheter hub;
an operation member guide space located between the first member and the second member, wherein a part of the catheter operation member is located in the operation member guide space; and
the operation member guide space is opened in a state in which the first member is separated from the second member to enable insertion of said part of the catheter operation member.

7. The catheter assembly according to claim 6, wherein:
the first member comprises an operation member exposure notch that exposes the catheter operation member from one end toward another end in the longitudinal direction; and
the first member and the second member comprise a pair of fixing mechanisms configured to be fixed to each other at a first end in the longitudinal direction on an outer side of the operation member exposure notch in a width direction, and at a second end in the longitudinal direction.

8. The catheter assembly according to claim 6, wherein:
the catheter operation member comprises a wing protruding from the operation member guide space; and

the wing is removable from the operation member guide space at one end in the longitudinal direction in a state in which the first member and the second member are assembled.

9. The catheter assembly according to claim 1, wherein:
the grip comprises a lower support member that supports a lower portion of the catheter when puncture is performed with the catheter and the inner needle;
the second member comprises an arrangement mechanism that rotatably and pivotally supports a shaft of the lower support member; and
the arrangement mechanism enables insertion of the lower support member by being opened in the assembling direction of the first member in a state in which the first member is separated from the second member in an axial direction of the shaft, and inhibits detachment of the shaft in a state in which the first member and the second member are assembled.

10. The catheter assembly according to claim 9, wherein:
the lower support member includes a supporting body portion that protrudes from the shaft to a point where the catheter extends and is configured to come into contact with the catheter; and
the second member has a bearing notch that is configured to pass extends through the supporting body portion when the lower support member is arranged in the arrangement mechanism.

11. The catheter assembly according to claim 1, wherein:
the inner needle hub is configured to be fixed to the second member, prior to attachment of the second member to the first member in the direction orthogonal to the longitudinal direction, as the needle assembly is placed on the second member in the direction orthogonal to the longitudinal direction.

12. A method of manufacturing a catheter assembly, the method comprising:
providing a needle assembly extending in a longitudinal direction and comprising:
a catheter hub holding the catheter, an inner needle inserted through the catheter and configured to be punctured into a treatment target,
an inner needle hub holding the inner needle, and
a safety member that is movable together with the catheter hub and configured to advance beyond a needle tip of the inner needle, wherein the safety member comprises:
a proximal extending portion extending in the longitudinal direction, and
a protruding portion that protrudes from the proximal extending portion in a direction different from the longitudinal direction, wherein the protruding portion is thinner than the proximal extending portion in a direction orthogonal to the longitudinal direction;
providing a grip that accommodates the needle assembly, wherein the grip is configured to accommodate at least a part of the safety member before puncture of the inner needle and until the safety member advances beyond the needle tip, and comprises a first member and a second member that are separable from one another in a direction orthogonal to a longitudinal direction of the grip;
placing the needle assembly on the second member in an assembling direction, thereby fixing the inner needle hub to the second member; and
after placing the needle assembly on the second member and fixing the inner needle hub to the second member, attaching the first member to the second member in the assembling direction such that the safety member is held by the grip, such that a safety guide space is located between the first member and the second member in the direction orthogonal to the longitudinal direction, and a part of the protruding portion is located in the safety guide space.

* * * * *